United States Patent [19]
Ryu et al.

[11] Patent Number: 6,096,930
[45] Date of Patent: Aug. 1, 2000

[54] HERBICIDAL CYCLOHEXANE-1,3-DIONE DERIVATIVES AND THEIR PREPARATION PROCESS

[75] Inventors: Eung Kul Ryu; Kyoung Mahn Kim; Jae Nyoung Kim; Jin Seog Kim, all of Daejeon, Rep. of Korea

[73] Assignee: Korea Research Institute of Chemical Technology, Daejeon, Rep. of Korea

[21] Appl. No.: 09/075,787

[22] Filed: May 12, 1998

Related U.S. Application Data

[62] Division of application No. 08/793,042, Jun. 18, 1997, abandoned.

Foreign Application Priority Data

Aug. 18, 1994 [KR] Rep. of Korea ................. 94-20420

[51] Int. Cl.$^7$ ...................................... C07C 45/46
[52] U.S. Cl. .......................... 568/437; 564/86; 564/88; 564/253; 564/257; 568/27; 568/28; 568/30; 568/31; 568/42; 568/43; 568/308; 568/309; 568/319; 568/322; 568/323; 568/424
[58] Field of Search .................. 564/86, 88, 253, 564/257; 568/27, 28, 30, 31, 42, 43, 308, 309, 319, 322, 323, 424, 437

[56] References Cited

U.S. PATENT DOCUMENTS

| | | | |
|---|---|---|---|
| 4,952,722 | 8/1990 | Serban et al. | 560/250 |
| 5,154,753 | 10/1992 | Meyer et al. | 71/121 |

OTHER PUBLICATIONS

Smith et al., 'Polyalkylbenzenes, etc.' Journal of the American Chemical Society, 73, 3843–3847, Aug. 1951.

March, J., Advanced Organic Chemistry, etc., McGraw–Hill, 413–416, 1968.

*Primary Examiner*—Peter O'Sullivan
*Attorney, Agent, or Firm*—Finnegan, Henderson, Farabow, Garrett & Dunner, L.L.P.

[57] ABSTRACT

The present invention relates to novel cyclohexane-1-3-dione derivatives of formula (1) useful as herbicides and plant-growth regulants,

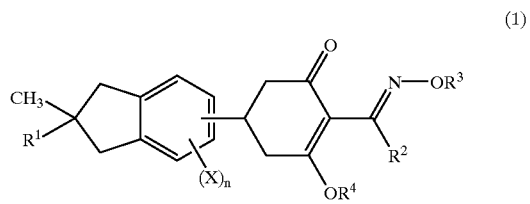

(1)

wherein X is selected from the group consisting of hydrogen, halogen, $C_1$–$C_6$ alkyl, $C_2$–$C_6$ alkoxy, $C_1$–$C_6$ haloalkyl, nitro, $C_1$–$C_6$ alkylthio, $C_1$–$C_6$ alkylsulfinyl, $C_1$–$C_6$ alkylsulfonyl, $C_1$–$C_6$ sulfamoyl, and N, N-di($C_1$–$C_6$ alkyl)sulfamoyl group; (X)n represents the number of X substituents which may be substituted on benzene ring, wherein n is 1, 2 or 3. Also, cyclohexyl moiety, one of the substituents on benzofuran ring, is substituted at C-4, C-5, C-6 or C-7 position on benzene ring; $R^1$ is selected from the group consisting of hydrogen and $C_1$–$C_6$ alkyl group; $R^2$ is selected from the group consisting of $C_1$–$C_6$ alkyl, $C_2$–$C_6$ alkenyl and $C_2$–$C_6$ alkynyl group; $R^3$ is selected from the group consisting of hydrogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkoxyalkyl, $C_2$–$C_6$ alkylthioalkyl, benzyl and $C_2$–$C_6$ haloalkanoyl group; $R^4$ is selected from the group consisting of hydrogen, alkali metal cation, alkaline earth metal cation, $C_1$–$C_4$ alkanoyl, $C_1$–$C_4$ haloalkanoyl and benzoyl group.

5 Claims, No Drawings

HERBICIDAL CYCLOHEXANE-1,3-DIONE DERIVATIVES AND THEIR PREPARATION PROCESS

This is a division of application Ser. No. 08/793,042 filed Jun. 18, 1997, now abandoned, which is a National Stage Application under 35 U.S.C. § 371 of International Application PCT/KR95/00092, all of which are incorporated herein by reference.

BACKGROUND OF THE INVENTION

1. Technical Field

The present invention relates to novel cyclohexane-1,3-dione derivatives of the following formula (1) useful as herbicides and plant-growth regulants.

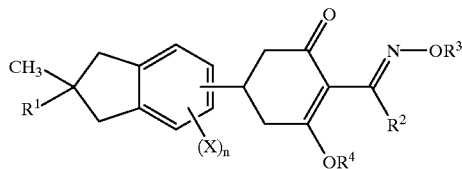

(1)

wherein,

X is selected from the group consisting of hydrogen, halogen, $C_1$~$C_6$ alkyl, $C_2$~$C_6$ alkoxy, $C_1$~$C_6$ haloalkyl, nitro, $C_1$~$C_6$ alkylthio, $C_1$~$C_6$ alkylsulfinyl, $C_1$~$C_6$ alkylsulfonyl, $C_1$~$C_6$ sulfamoyl, and N, N-di($C_1$~$C_6$ alkyl) sulfamoyl group;

(X)n represents the number of X substituents which may be substituted on benzene ring, wherein n is 1, 2 or 3. Also, cyclohexyl moiety, one of the substituents on benzofuran ring, is substituted at C-4, C-5, C-6 or C-7 position on benzen ring;

$R^1$ is selected from the group consisting of hydrogen and $C_1$~$C_6$ alkyl group;

$R^2$ is selected from the group consisting of $C_1$~$C_6$ alkyl, $C_2$~$C_6$ alkenyl and $C_2$~$C_6$ alkynyl group;

$R^3$ is selected from the group consisting of hydrogen, $C_1$~$C_6$ alkyl, $C_1$~$C_6$ haloalkyl, $C_2$~$C_6$ alkenyl, $C_2$~$C_6$ haloalkenyl, $C_2$~$C_6$ alkoxyalkyl, $C_2$~$C_6$ alkylthioalkyl, benzyl and $C_2$~$C_6$ haloalkanoyl group;

$R^4$ is selected from the group consisting of hydrogen, alkali metal cation, alkaline earth metal cation, $C_1$~$C_4$ alkanoyl, $C_1$~$C_4$ haloalkanoyl and benzoyl group.

DESCRIPTION OF THE RELATED ART

Cyclohexane-1,3-dione derivatives and their herbicidal activity were already known in the arts. For example, Alloxidim-sodium (Australian Patent No. 464,655; British Patent No. 1,461,170; U.S. Pat. No. 3,950,420) and Sethoxydim (German Patent No. 2,822,304) have been commercially used as herbicides. Also cyclohexane-1,3-dione derivatives having substituted phenyl group (U.S. Pat. No. 4,639,267 and U.S. Pat. No. 4,652,303) have been known. But cyclohexane-1,3-dione derivatives having 2,3-dihydroindanyl group such as the above formula(1) compound of the present invention have not been known.

Therefore, the present inventors have made efforts to develop new herbicidal compounds which have powerful herbicidal activity and good selectivity, especially useful for selective control barnyardgrass species in upland and paddy rice.

SUMMARY OF THE INVENTION

The object of the present invention is to provide novel compounds of the above formular (1) and its preparation processes.

Another object is to provide herbicidal composition with strong herbicidal activity and good selectivity, especially for paddy rice and broad leaved plant, containing a compound of formula (1) as active ingredient.

DETAILED DESCRIPTION OF THE INVENTION

The present invention is identified as cyclohexane-1,3-dione derivatives of the following formula (1).

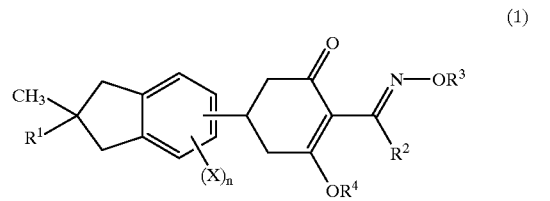

(1)

wherein, (X)n, $R^1$, $R^2$, $R^3$ and $R^4$ are respectively defined as described above.

In the formula (1) according to the present invention the preferred compounds are as follows: X is selected from the group consisting of hydrogen, halogen and $C_1$~$C_6$ alkyl group; n is 1, 2 or 3; $R^1$ is selected from the group consisting of hydrogen and $C_1$~$C_6$ alkyl group; $R^2$ is selected from the group consisting of $C_1$~$C_6$ alkyl group; $R^3$ is selected from the group consisting of hydrogen, $C_1$~$C_6$ alkyl, $C_2$~$C_6$ alkenyl and $C_2$~$C_6$ haloalkenyl group; $R^4$ is hydrogen.

Among the compounds of the present invention, the compounds of the following formula (1-a), (1-b) and (1-c) are especially preferred.

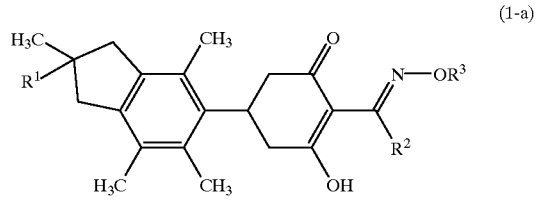

(1-a)

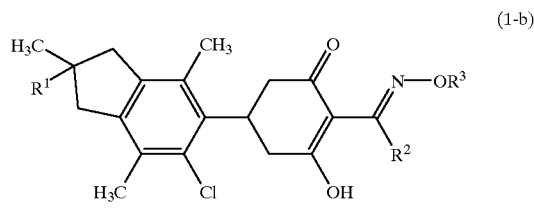

(1-b)

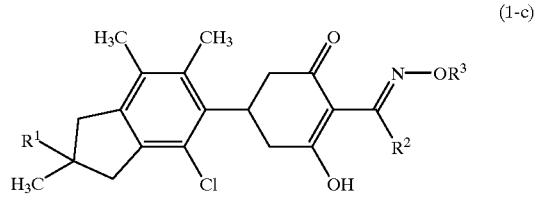

(1-c)

wherein $R^1$, $R^2$ and $R^3$ are respectively defined as described above.

Typical compounds of the above formula (1) according to the present invention are as follows:

5-(2,2,4,6,7-Pentamethylindan-5-yl)-2-[1-(allyloxyimino)propyl]-3-hydroxycyclohex-2-en-1-one;

5-(2-Ethyl-2,4,5,7-tetramethylindan-6-yl)-2-[1-(allyloxyimino)propyl]-3-hydroxycyclohex-2-en-1-one;

5-(6-Chloro-2,2,4,7-tetramethylindan-5-yl)-2-[1-(ethoxyimino)butyl]-3-hydroxycyclohex-2-en-1-one;

5-(6-Chloro-2-ethyl-2,4,7-trimethylindan-5-yl)-2-[1-(ethoxyimino)propyl]-3-hydroxycyclohex-2-en-1-one;

5-(7-Chloro-2,2,4,5-tetramethylindan-6-yl)-2-[1-(ethoxyimino)butyl]-3-hydroxycyclohex-2-en-1-one;

5-(7-Chloro-2-ethyl-2,4,5-trimethylindan-6-yl)-2-[1-(ethoxyimino)propyl]-3-hydroxycyclohex-2-en-1-one;

Where the compounds of the formula (1) can exhibit tautomerism, the formula is intended to cover all tautomers, the present invention encompasses within its scope all the tautomers and their mixtures of compound of the formula (1).

The compounds of the formula (1) of which $R^4$ is hydrogen may exist in any one of four tautomeric forms as shown below.

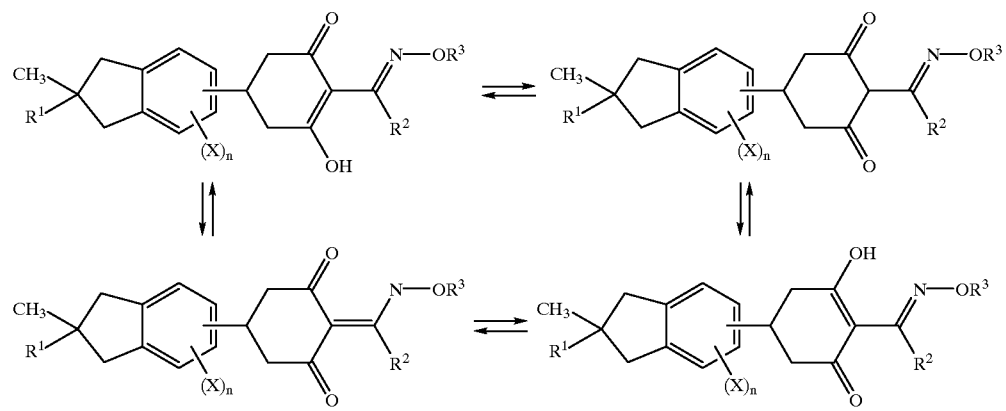

wherein, $(X)_n$, $R^1$, $R^2$ and $R^3$ are respectively defined as described above.

Processes for preparing the compounds (1) and their intermediates according to the present invention are as shown in reaction Scheme A~D.

A processes for the preparation of compounds (1) is shown in reaction Scheme A.

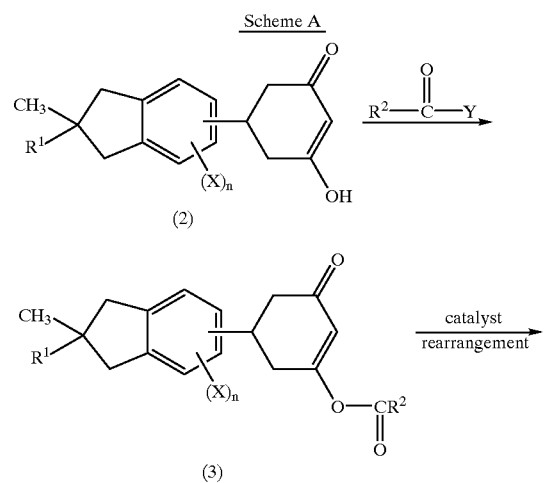

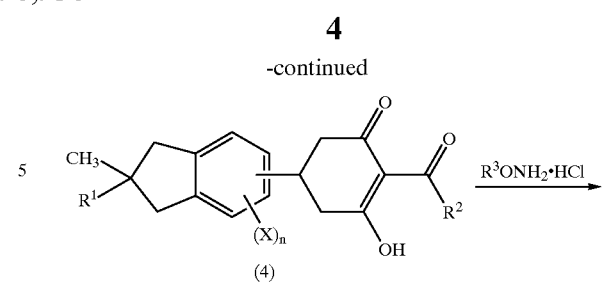

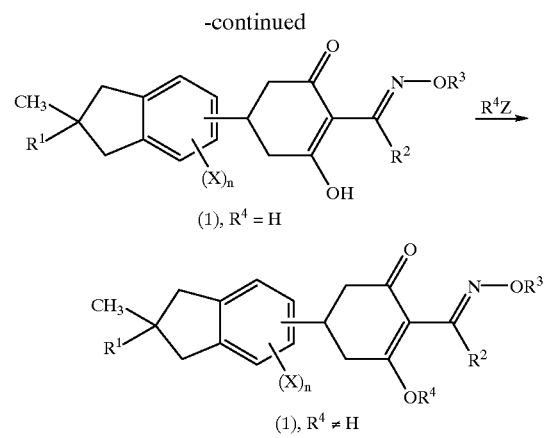

wherein, $(X)_n$, $R^1$, $R^2$, $R^3$ and $R^4$ are respectively defined as described above; Y is selected from the group consisting of halogen and —O—CO—$R^2$ group; Z is selected from the group consisting of halogen and hydroxy group.

According to the Scheme A, cyclohexane-1,3-dione derivatives of the above formula (2) are reacted with acid halide or acid anhydride in an inert organic solvent to obtain the cyclohexanone ester of the above formula (3).

The compound (3) is rearranged in the presence of catalyst such as pyridine, 4-(dimethylamino)pyridine or 1,8-diazabicylo[5.4.0]undec-7-ene, etc. and an inert organic solvent such as benzene, toluene or xylene, etc. to obtain 2-acyl-1,3-cyclohexandione derivatives of the above formula (4).

The compound (4) is reacted with substituted hydroxylamine hydrochloride ($R^3ONH_2$.HCl) in a base catalyst such as carbonate, acetate or hydroxide containing alkai metal or alkalin earth metal, and an alcohol solvent to obtain the compound of the above formula (1, $R^4$=hydrogen) according to the present invention.

To obtain the compound of the above formula (1, $R^4 \neq$ hydrogen), the compound (1, $R^4$=hydrogen) is reacted with alkali metal hydroxide, alkalin earth metal hydroxide, acyl halide, haloacyl halide or benzoyl halide, etc.

Also, the compounds of the above formula (2) and (4) are novel compounds.

And a process for preparing the novel cyclohexane-1,3-dione derivatives of the above formula (2) is as follows:

Scheme B

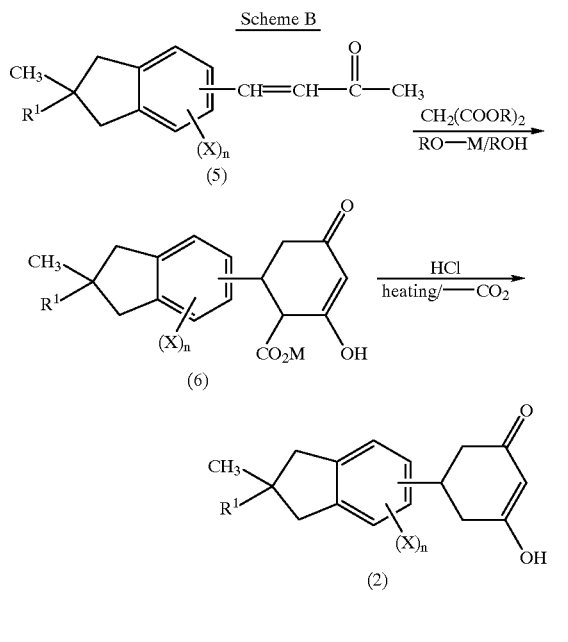

wherein, (X)n and $R^1$ are respectively defined as described above; R is selected from the group of consisting of $C_1$~$C_4$ alkyl group; M is selected from the group of consisting of alkali metal and alkalin earth metal.

According to the Scheme B, benzalacetone derivatives of the above formula (5) are reacted with malonic ester in the presence of alkoxide containg alkali metal or alkalin earth metal in anhydrous alcohol solvent at the boiling temperature of alcohol solvent to obtain cyclohexan-1,3-dione-4-carboxylic acid of the above formula (6). The compound (6) is decarboxylated using strong acid such as hydrochloric acid or sulfuric acid, etc. to obtain the compound of the above formula (2).

And a process for preparing the above formula (5) is as follows:

Scheme C

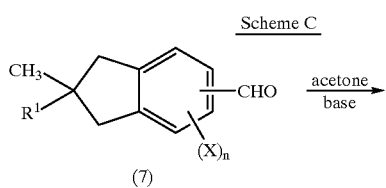

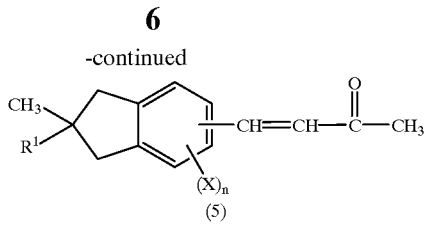

wherein, (X)n and $R^1$ are respectively defined as described above.

According to the Scheme C, substituted benzaldehyde derivatives of the formula (7) are reacted with acetone in the presence of base catalyst such as alkali metal hydroxide or alkalin earth metal hydroxide in water or a mixture of water and alcohol to obtain the compound of the above formula (5).

And a process for preparing the above formula (7) is as follows:

Scheme D

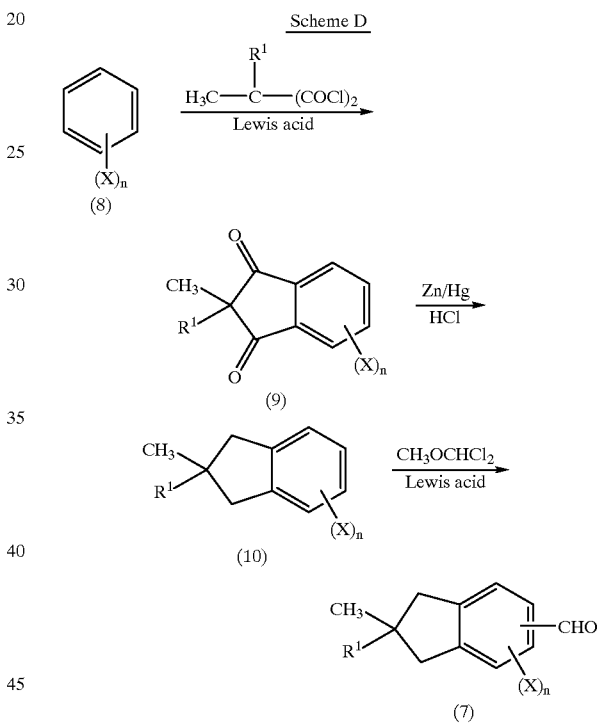

wherein, (X)n and $R^1$ are respectively defined as described above.

According to the scheme D, benzene derivatives of the formula (8) are reacted with malonyl halide in the presence of Lewis acid such as $AlCl_3$, $FeCl_3$, $TiCl_4$ or $BF_3.OEt_2$, etc., called Fiedel-Craft acylation, to obtain 2-methyl-2-alkylindan-1,3-dione derivatives of the above formula (9).

And the compound (9) is reduced by hydrochloric acid in zinc-mercury alloy (Zn/Hg) to obtain 2-methyl-2-alkylindane derivatives of the above formula (10).

And the compound (10) is reacted with α,α-dichloromethylmethylether in the presence of Lewis acid to obtaind the above formula (7). The process of introducing aldehyde group into the compound of formula (10) was disclosed in Organic Synthesis, Coll. Vol. V. 49.

Aforesaid preparation processes consistitute the major object of the present invention.

Novel compounds of the above formula (1), which are divided into formula (1-a), (1-b) and (1-c), are typically listed in following Table 1~3 respectively.

TABLE 1

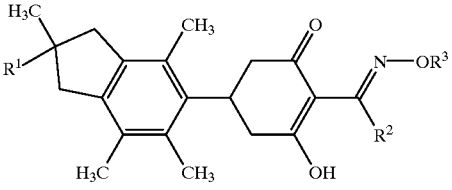

(1-a)

| Compound No. | R¹ | R² | R³ | mp (° C.) | ¹H NMR (ppm) |
|---|---|---|---|---|---|
| 1 | CH₃ | C₂H₅ | CH₃ | | 1.13(t, 3H), 1.18(s, 6H), 2.10(s, 3H), 2.30(s, 6H), 2.50~3.40(m, 11H), 3.90(s, 3H), 10.8(br, 1H). |
| 2 | CH₃ | C₂H₅ | C₂H₅ | | 1.10~1.52(m, 6H), 1.18(s, 6H), 2.10(s, 3H), 2.30(s, 6H), 2.50~3.40(m, 11H), 4.0(q, 2H), 10.8(br, 1H). |
| 3 | CH₃ | C₂H₅ | CH₂=CHCH₂ | | 1.20(t, 3H), 1.21(s, 6H), 2.17(s, 3H), 2.25(s, 3H), 2.75(s, 3H), 2.50~3.40(m, 10H), 3.80~4.0(m, 1H), 4.6(d, 2H), 5.5(dd, 2H), 5.8~6.2(m, 1H), 10.8(br, 1H). |
| 4 | CH₃ | C₂H₅ | ClCH=CHCH₂ | | 1.20(t, 3H), 1.20(s, 6H), 2.17(s, 3H), 2.25(s, 3H), 2.75(s, 3H), 2.50~3.40(m, 11H), 3.5(d, 1H), 3.8(d, 1H), 6.2(m, 2H), 10.8(br, 1H). |
| 5 | CH₃ | C₂H₅ | CH₂=C(CH₃)CH₂ | | 1.20(t, 3H), 1.21(s, 6H), 1.52(d, 3H), 2.17(s, 3H), 2.40(s, 6H), 2.50~3.40(m, 11H), 4.6(m, 2H), 5.1~5.8(m, 2H), 10.8(br, 1H). |
| 6 | CH₃ | n-C₃H₇ | CH₃ | | 0.95~1.50(m, 5H), 1.21(s, 6H), 2.10(s, 3H), 2.30(s, 6H), 2.50~3.40(m, 11H), 3.90(s, 3H), 10.8(br, 1H). |
| 7 | CH₃ | n-C₃H₇ | C₂H₅ | | 0.98~1.62(m, 7H), 1.23(s, 6H), 2.10(s, 3H), 2.30(s, 6H), 2.50~3.40(m, 11H), 4.2(q, 2H), 10.8(br, 1H). |
| 8 | CH₃ | n-C₃H₇ | CH₂=CHCH₂ | | 0.96~1.82(m, 5H), 1.21(s, 6H), 2.17(s, 3H), 2.25(s, 3H), 2.75(s, 3H), 2.50~3.40(m, 10H), 3.80~4.0(m, 1H), 4.6(d, 2H), 5.5(dd, 2H), 5.8~6.2(m, 1H), 10.8(br, 1H). |
| 9 | CH₃ | n-C₃H₇ | ClCH=CHCH₂ | | 0.98~1.82(m, 5H), 1.20(s, 6H), 2.17(s, 3H), 2.25(s, 3H), 2.75(s, 3H), 2.50~3.40(m, 11H), 3.5(d, 1H), 3.8(d, 1H), 6.2(m, 2H), 10.8(br, 1H). |
| 10 | CH₃ | n-C₃H₇ | CH₂=C(CH₃)CH₂ | | 0.98~1.82(m, 5H), 1.21(s, 6H), 1.52(d, 3H), 2.17(s, 3H), 2.40(s, 6H), 2.50~3.40(m, 11H), 4.6(m, 2H), 5.1~5.8(m, 2H), 10.8(br, 1H). |
| 11 | C₂H₅ | C₂H₅ | CH₃ | Oil | 0.90(t, 3H), 1.10(s, 3H), 1.18(t, 3H), 1.21(t, 3H), 1.52(q, 2H), 2.17(s, 3H), 2.30(s, 6H), 2.52~3.47(m, 11H), 3.90(s, 3H), 11.2(br, 1H). |
| 12 | C₂H₅ | C₂H₅ | C₂H₅ | 57~59 | 0.90(t, 3H), 1.10(s, 3H), 1.18(t, 3H), 1.52(q, 2H), 2.17(s, 3H), 2.30(s, 6H), 2.52~3.47(m, 11H), 4.20(q, 2H), 11.2(br, 1H). |
| 13 | C₂H₅ | C₂H₅ | CH₂=CHCH₂ | 64~65 | 0.90(t, 3H), 1.10(s, 3H), 1.18(t, 3H), 1.52(q, 2H), 2.17(s, 3H), 2.25(s, 3H), 2.30(s, 3H), 2.52~2.50(m, 6H), 3.05~3.47(m, 4H), 3.80~4.05(m, 1H), 4.5(d, 2H), 5.15~5.50(m, 2H), 5.6~6.2(m, 1H), 11.2(br, 1H). |
| 14 | C₂H₅ | C₂H₅ | ClCH=CHCH₂ | 63~66 | 0.90(t, 3H), 1.10(s, 3H), 1.18(t, 3H), 1.52(q, 2H), 2.17(s, 3H), 2.25(s, 3H), 2.30(s, 3H), 2.62~3.75(m, 11H), 4.6(d, 1H), 4.8(d, 1H), 5.95~6.50(m, 2H), 11.2(br, 1H). |
| 15 | C₂H₅ | C₂H₅ | CH₂=C(Cl)CH₂ | 89~91 | 0.90(t, 3H), 1.10(s, 3H), 1.18(t, 3H), 1.52(q, 2H), 2.17(s, 3H), 2.25(s, 3H), 2.30(s, 3H), 2.62~3.75(m, 11H), 4.65(s, 2H), 5.50(m, 2H), 11.2(br, 1H). |

TABLE 1-continued (1-a)

$$\text{structure (1-a)}$$

| Compound No. | $R^1$ | $R^2$ | $R^3$ | mp (° C.) | $^1$H NMR (ppm) |
|---|---|---|---|---|---|
| 16 | $C_2H_5$ | n-$C_3H_7$ | $CH_3$ | Oil | 0.90(t, 3H), 1.10(s, 3H), 1.18(t, 3H), 1.21(t, 3H), 1.52(q, 2H), 1.82(q, 2H), 2.17(s, 3H), 2.30(s, 6H), 2.52~3.47(m, 11H), 3.90(s, 3H), 11.2(br, 1H). |
| 17 | $C_2H_5$ | n-$C_3H_7$ | $C_2H_5$ | Oil | 0.90(t, 3H), 1.10(s, 3H), 1.18(t, 3H), 1.21(t, 3H), 1.52(q, 2H), 1.82(q, 2H), 2.17(s, 3H), 2.30(s, 6H), 2.52~3.47(m, 11H), 4.20(q, 2H), 11.2(br, 1H). |
| 18 | $C_2H_5$ | n-$C_3H_7$ | $CH_2$=CHCH$_2$ | Oil | 0.90(t, 3H), 1.10(s, 3H), 1.18(t, 3H), 1.21(t, 3H), 1.52(q, 2H), 1.82(q, 2H), 2.17(s, 3H), 2.25(s, 3H), 2.30(s, 3H), 2.52~2.50(m, 6H), 3.05~3.47(m, 4H), 3.80~4.05(m, 1H), 4.5(d, 2H), 5.15~5.50(m, 2H), 5.6~6.2(m, 1H), 11.2(br, 1H). |
| 19 | $C_2H_5$ | n-$C_3H_7$ | ClCH=CHCH$_2$ | | 0.90(t, 3H), 1.10(s, 3H), 1.18(t, 3H), 1.21(t, 3H), 1.52(q, 2H), 1.82(q, 2H), 2.17(s, 3H), 2.25(s, 3H), 2.30(s, 3H), 2.62~3.75(m, 11H), 4.6(d, 1H), 4.8(d, 1H), 5.95~6.50(m, 2H), 11.2(br, 1H). |
| 20 | $C_2H_5$ | n-$C_3H_7$ | $CH_2$=C(Cl)CH$_2$ | | 0.90(t, 3H), 1.10(s, 3H), 1.18(t, 3H), 1.21(t, 3H), 1.52(q, 2H), 1.82(q, 2H), 2.17(s, 3H), 2.25(s, 3H), 2.30(s, 3H), 2.62~3.75(m, 11H), 4.65(s, 2H), 5.50(m, 2H), 11.2(br, 1H). |

TABLE 2

(1-b)

$$\text{structure (1-b)}$$

| Compound No. | $R^1$ | $R^2$ | $R^3$ | mp (° C.) | $^1$H NMR (ppm) |
|---|---|---|---|---|---|
| 21 | $CH_3$ | $C_2H_5$ | $CH_3$ | Oil | 1.15(s, 6H), 1.16(t, 3H), 2.2(s, 6H), 2.45~2.9(m, 9H), 3.1(q, 2H), 3.92(s, 3H), 10.5(br, 1H). |
| 22 | $CH_3$ | $C_2H_5$ | $C_2H_5$ | Oil | 1.0(t, 3H), 1.15(s, 6H), 1.32(t, 3H), 2.2(s, 6H), 2.50~3.45(m, 10H), 3.80(s, 1H), 4.0(q, 2H), 11.2(br, 1H). |
| 23 | $CH_3$ | $C_2H_5$ | $CH_2$=CHCH$_2$ | Oil | 1.15(s, 6H), 1.16(t, 3H), 2.2(s, 6H), 2.45~2.9(m, 9H), 4.60(dd, 2H), 5.1~5.6(m, 3H), 10.5(br, 1H). |
| 24 | $CH_3$ | $C_2H_5$ | $CH_2$=C(CH$_3$)CH$_2$ | Oil | 1.15(s, 6H), 1.16(t, 3H), 1.56(d, 3H), 2.2(s, 6H), 2.45~2.9(m, 9H), 4.60(dd, 2H), 5.1~5.6(m, |

TABLE 2-continued

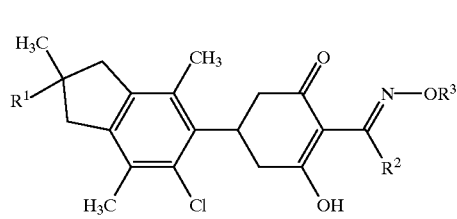

(1-b)

| Compound No. | R¹ | R² | R³ | mp (° C.) | ¹H NMR (ppm) |
|---|---|---|---|---|---|
| 25 | CH₃ | n-C₃H₇ | CH₃ | Oil | 2H), 10.5(br, 1H). 0.97(t, 3H), 1.15(s, 6H), 1.65(q, 2H), 2.2(s, 6H), 2.45~2.9(m, 9H), 3.1(q, 2H), 3.92(s, 3H), 10.5(br, 1H). |
| 26 | CH₃ | n-C₃H₇ | C₂H₅ | Oil | 1.0(t, 3H), 1.15(s, 6H), 1.32(t, 3H), 1.68(q, 2H), 2.2(s, 6H), 2.50~3.45 (m, 10H), 3.80(s, 1H), 4.0(q, 2H), 10.8(br, 1H). |
| 27 | CH₃ | n-C₃H₇ | CH₂=CHCH₂ | Oil | 0.97(t, 3H), 1.15(s, 6H), 1.65(q, 2H), 2.2(s, 6H), 2.45~2.9(m, 9H), 4.60(dd, 2H), 5.1~5.6(m, 3H), 10.5 (br, 1H). |
| 28 | CH₃ | n-C₃H₇ | CH₂=C(CH₃)CH₂ | Oil | 0.97(t, 3H), 1.15(s, 6H), 1.65(q, 2H), 2.2(s, 6H), 2.45~2.9(m, 9H), 4.60(dd, 2H), 5.1~5.6(m, 2H), 10.5 (br, 1H). |
| 29 | C₂H₅ | C₂H₅ | CH₃ | 47~48 | 0.9(t, 3H), 1.07(s, 3H), 1.16(t, 3H), 1.50(q, 2H), 2.2(s, 6H), 2.45~2.9(m, 11H), 3.1(q, 2H), 3.92(s, 3H), 10.5 (br, 1H). |
| 30 | C₂H₅ | C₂H₅ | C₂H₅ | Oil | 0.9(t, 3H), 1.05(s, 3H), 1.12(t, 3H), 1.15(t, 3H), 1.5(q, 2H), 2.2(s, 6H), 2.40~2.85(m, 11H), 3.5~4.0(m, 1H), 4.15(q, 2H), 5.30(s, 1H), 9.5(br, 1H). |
| 31 | C₂H₅ | C₂H₅ | CH₂=CHCH₂ | 41~43 | 0.9(t, 3H), 1.07(s, 3H), 1.16(t, 3H), 1.50(q, 2H), 2.2(s, 6H), 2.45~2.9(m, 11H), 3.1(q, 2H), 4.55(dd, 2H), 5.1~5.25(m, 2H), 10.5(br, 1H). |
| 32 | C₂H₅ | C₂H₅ | ClCH=CHCH₂ | 40~42 | 0.9(t, 3H), 1.07(s, 3H), 1.16(t, 3H), 1.50(q, 2H), 2.2(s, 6H), 2.45~2.9(m, 11H), 3.1(q, 2H), 4.55(m, 2H), 5.1~5.25(m, 2H), 10.5(br, 1H). |
| 33 | C₂H₅ | n-C₃H₇ | CH₃ | Oil | 0.9(t, 3H), 1.00(s, 3H), 1.10(s, 3H), 1.16(t, 3H), 1.50(q, 2H), 1.70(q, 2H), 2.2(s, 6H), 2.45~2.9(m, 11H), 3.1(q, 2H), 3.92(s, 3H), 10.5(br, 1H). |
| 34 | C₂H₅ | n-C₃H₇ | C₂H₅ | 39~41 | 1.0(t, 3H), 1.15(s, 6H), 1.32(t, 3H), 1.68(q, 2H), 2.2(s, 6H), 2.50~3.45 (m, 10H), 3.80(s, 1H), 4.0(q, 2H), 10.8(br, 1H). |
| 35 | C₂H₅ | n-C₃H₇ | CH₂=CHCH₂ | Oil | 0.9(t, 3H), 1.00(s, 3H), 1.10(s, 3H), 1.16(t, 3H), 1.50(q, 2H), 1.70(q, 2H), 2.2(s, 6H), 2.45~2.9(m, 11H), 3.1(q, 2H), 4.55(dd, 2H), 5.1~5.25 (m, 3H), 10.5(br, 1H). |
| 36 | C₂H₅ | n-C₃H₇ | ClCH=CHCH₂ | Oil | 0.9(t, 3H), 1.00(s, 3H), 1.10(s, 3H), 1.16(t, 3H), 1.50(q, 2H), 1.70(q, 2H), 2.2(s, 6H), 2.45~ 2.9(m, 11H), 3.1(q, 2H), 4.55(dd, 2H), 5.1~5.25(m, 2H), 10.5(br, 1H). |
| 37 | C₂H₅ | n-C₃H₇ | CH₂=C(Cl)CH₂ | 42~43 | 0.9(t, 3H), 1.00(s, 3H), 1.10(s, 3H), 1.16(t, 3H), 1.50(q, 2H), 1.70(q, 2H), 2.2(s, 6H), 2.45~ 2.9(m, 11H), 3.1(q, 2H), 4.5(s, 2H), 5.5(s, 2H), 10.5(br, 1H). |

TABLE 3

(1-c)

| Compound No. | R¹ | R² | R³ | mp (° C.) | ¹H NMR (ppm) |
|---|---|---|---|---|---|
| 38 | CH₃ | C₂H₅ | CH₃ | Oil | 1.15(s, 6H), 1.16(t, 3H), 2.17(s, 3H), 2.31(s, 3H), 2.45~2.9(m, 9H), 3.1(q, 2H), 3.92(s, 3H), 10.5(br, 1H). |
| 39 | CH₃ | C₂H₅ | C₂H₅ | Oil | 1.15(s, 6H), 1.16(t, 3H), 1.65(q, 2H), 2.17(s, 3H), 2.31(s, 3H), 2.45~2.9(m, 9H), 3.1(q, 2H), 4.12(s, 3H), 10.5(br, 1H). |
| 40 | CH₃ | C₂H₅ | CH₂=CHCH₂ | Oil | 1.15(s, 6H), 1.16(t, 3H), 2.17(s, 3H), 2.31(s, 3H), 2.45~2.9(m, 9H), 4.60(dd, 2H), 5.1~5.6(m, 3H), 10.5(br, 1H). |
| 41 | CH₃ | C₂H₅ | CH₂=C(CH₃)CH₂ | Oil | 1.15(s, 6H), 1.16(t, 3H), 1.56(d, 3H), 2.17(s, 3H), 2.31(s, 3H), 2.45~2.9(m, 9H), 4.60(dd, 2H), 5.1~5.6(m, 2H), 10.5(br, 1H). |
| 42 | CH₃ | n-C₃H₇ | CH₃ | Oil | 0.97(t, 3H), 1.15(s, 6H), 1.65(q, 2H), 2.17(s, 3H), 2.31(s, 3H), 2.45~2.9(m, 9H), 3.1(q, 2H), 3.92(s, 3H), 10.5(br, 1H). |
| 43 | CH₃ | n-C₃H₇ | C₂H₅ | Oil | 1.0(t, 3H), 1.15(s, 6H), 1.32(t, 3H), 1.68(q, 2H), 2.12(s, 3H), 2.21(s, 3H), 2.50~3.45(m, 10H), 3.80(s, 1H), 4.0(q, 2H), 10.8(br, 1H). |
| 44 | CH₃ | n-C₃H₇ | CH₂=CHCH₂ | Oil | 0.97(t, 3H), 1.15(s, 6H), 1.65(q, 2H), 2.17(s, 3H), 2.31(s, 3H), 2.45~2.9(m, 9H), 4.60(dd, 2H), 5.1~5.6(m, 3H), 10.5(br, 1H). |
| 45 | CH₃ | n-C₃H₇ | CH₂=C(CH₃)CH₂ | Oil | 0.97(t, 3H), 1.15(s, 6H), 1.65(q, 2H), 2.17(s, 3H), 2.31(s, 3H), 2.45~2.9(m, 9H), 4.60(dd, 2H), 5.1~5.6(m, 2H), 10.5(br, 1H). |
| 46 | C₂H₅ | C₂H₅ | CH₃ | Oil | 0.9(t, 3H), 1.07(s, 3H), 1.16(t, 3H), 1.50(q, 2H), 2.12(s, 3H), 2.22(s, 3H), 2.45~2.9(m, 11H), 3.1(q, 2H), 3.92(s, 3H), 10.5(br, 1H). |
| 47 | C₂H₅ | C₂H₅ | C₂H₅ | 93~94 | 0.9(t, 3H), 1.07(s, 3H), 1.16~1.21(m, 6H), 1.50(q, 2H), 2.12(s, 3H), 2.22(s, 3H), 2.45~2.9(m, 11H), 3.1(q, 2H), 4.12(s, 3H), 10.5(br, 1H). |
| 48 | C₂H₅ | C₂H₅ | CH₂=CHCH₂ | | 0.9(t, 3H), 1.07(s, 3H), 1.16(t, 3H), 1.50(q, 2H), 2.12(s, 3H), 2.22(s, 3H), 2.45~2.9(m, 11H), 3.1(q, 2H), 4.55(dd, 2H), 5.1~5.25(m, 2H), 10.5(br, 1H). |
| 49 | C₂H₅ | C₂H₅ | ClCH=CHCH₂ | | 0.9(t, 3H), 1.07(s, 3H), 1.16(t, 3H), 1.50(q, 2H), 2.12(s, 3H), 2.22(s, 3H), 2.45~2.9(m, 11H), 3.1(q, 2H), 4.55(m, 2H), 5.1~5.25(m, 2H), 10.5(br, 1H). |
| 50 | C₂H₅ | C₂H₅ | CH₂=C(Cl)CH₂ | 94~96 | 0.9(t, 3H), 1.07(s, 3H), 1.16(t, 3H), 1.50(q, 2H), 2.12(s, 3H), 2.22(s, 3H), 2.45~2.9(m, 11H), 3.1(q, 2H), 4.5(s, 2H), 5.5(s, 2H), 10.5(br, 1H). |
| 51 | C₂H₅ | n-C₃H₇ | CH₃ | Oil | 0.9(t, 3H), 1.00(s, 3H), 1.10(s, 3H), 1.16(t, 3H), 1.50(q, 2H), 1.70(q, 2H), 2.12(s, 3H), 2.22(s, 3H), 2.45~2.9(m, 11H), 3.1(q, 2H), 3.92(s, 3H), 10.5(br, 1H). |
| 52 | C₂H₅ | n-C₃H₇ | C₂H₅ | 80~82 | 1.0(t, 3H), 1.15(s, 6H), 1.32(t, |

TABLE 3-continued (1-c)

[Structure: indane with H3C, CH3, R1, H3C substituents, Cl, connected to cyclohexenone with OH, N—OR3, R2 groups]

| Compound No. | R¹ | R² | R³ | mp (° C.) | ¹H NMR (ppm) |
|---|---|---|---|---|---|
| | | | | | 3H), 1.68(q, 2H), 2.12(s, 3H), 2.21(s, 3H), 2.50~3.45(m, 10H), 3.80(s, 1H), 4.0(q, 2H), 10.8(br, 1H). |
| 53 | $C_2H_5$ | $n\text{-}C_3H_7$ | $CH_2{=}CHCH_2$ | 67~69 | 0.9(t, 3H), 1.00(s, 3H), 1.10(s, 3H), 1.16(t, 3H), 1.50(q, 2H), 1.70(q, 2H), 2.12(s, 6H), 2.22(s, 3H), 2.45~2.9(m, 11H), 3.1(q, 2H), 4.55(dd, 2H), 5.1~5.25(m, 3H), 10.5(br, 1H). |
| 54 | $C_2H_5$ | $n\text{-}C_3H_7$ | $ClCH{=}CHCH_2$ | | 0.9(t, 3H), 1.00(s, 3H), 1.10(s, 3H), 1.16(t, 3H), 1.50(q, 2H), 1.70(q, 2H), 2.12(s, 6H), 2.22(s, 3H), 2.45~2.9(m, 11H), 3.1(q, 2H), 4.55(dd, 2H), 5.1~5.25(m, 2H), 10.5(br, 1H). |
| 55 | $C_2H_5$ | $n\text{-}C_3H_7$ | $CH_2{=}C(Cl)CH_2$ | | 0.9(t, 3H), 1.00(s, 3H), 1.10(s, 3H), 1.16(t, 3H), 1.50(q, 2H), 1.70(q, 2H), 2.12(s, 6H), 2.22(s, 3H), 2.45~2.9(m, 11H), 3.1(q, 2H), 4.5(s, 2H), 5.5(s, 2H), 10.5(br, 1H). |

Processes for preparing the present compounds of the formula (1) and the intermediates are illustrated further in the following examples.

EXAMPLE 1

5-(2,2,4,6,7-Pentamethylindan-5-yl)-2-[1-(allyloxyimino)propyl]-3-hydroxycyclohex-2-en-1-one.

i) 2,2,4,6,7-Pentamethylindan-1,3-dione.

To a mixture of 21.5 ml of 1,2,4-trimethylbenzene and 24.1 g of dimethylmalonyl chloride in 150 ml of dry dichloromethane was added slowly 38 mg of $AlCl_3$ under the current of nitrogen gas at −10° C. The reaction mixture was stirred at room temperature for 2 hours, quenched with 200 g of ice, and separated the organic layer. The aqueous layer was extracted with dichloromethane. The combined organic layer was dried over anhydrous magnesium sulfate, filtered and evaporated under reduced pressure. The residue was purified by silica-gel column chromatography to afford 28.9 g of the title compound as a yellow solid.

Yield: 75%
mp: 58~60° C.
¹H NMR(CDCl₃): δ 1.15(s, 6H), 2.40(s, 3H), 2.6(s, 6H), 7.02(s, 1H)

ii) 2,2,4,6,7-Pentamethylindane

To a mixture of 100 g of 7% Zn/Hg in 200 ml of 20% hydrochloric acid and 70 ml of ethanol was added 22.32 g of the 2,2,4,6,7-pentamethylindan-1,3-dione with stirring. After refluxing for 6 hours, the reaction mixture was added 100 ml of benzene and refluxed for 1 hour. The reaction mixture was cooled to room temperature and extracted with diethyl ether. The combined organic layer was dried over anhydrous magnesium sulfate, filtered and evaporated under reduced pressure. The residue was purified by silica-gel column chromatography to afford 15.67 g of the title compound as yellow oil.

Yield: 81%
¹H NMR(CDCl₃): δ 1.10(s, 6H), 2.05(s, 3H), 2.10(s, 3H), 2.55(s, 4H), 7.02(s, 1H)

iii) 2,2,4,6,7-Pentamethylindan-5-carboxaldehyde

To a solution of 24.5 g of the 2,2,4,6,7-pentamethylindane in 100 ml of dry dichloromethane was continuously added 18.5 ml of α,α-dichloromethyl methyl ether and 17.6 ml of $TiCl_4$ at 0° C. The reaction mixture was stirred at room temperature for 2 hours, quenched with 200 ml of water, and separated the organic layer. The aqueous layer was extracted with dichloromethane. The combined organic layer was dried over magnesium sulfate, filtered and evaporated under reduced pressure. The residue was purified by silica-gel column chromatography to afford 26.8 g of the title compound as yellow solid.

yield: 95%
mp: 61~62° C.
¹H NMR(CDCl₃): δ 115(s, 6H), 2.10(s, 3H), 2.30(s, 3H), 2.35(s, 3H), 2.70(s, 4H), 10.5(s, 1H)

iv) 4-(2,2,4,6,7-Pentamethylindan-5yl)-3-buten-2-one

To a solution of 26.8 g of the 2,2,4,6,7-pentamethylindan-5-carboxaldehyde in 93 ml of absolute acetone was added 46 ml of water and 50 g of 2% NaOH. After refluxing for 20 hours, the solution was acidified with 2N HCl and extracted with diethyl ether. The organic layer was dried over anhydrous magnesium sulfate, filtered and evaporated under reduced pressure. The residue was purified by silica-gel column chromatography to afford 25.36 g of the title compound as yellow solid.

yield: 79%

¹H NMR(CDCl₃): δ 1.20(s, 6H), 2.20(s, 3H), 2.25(s, 6H), 2.35(s, 3H), 2.70(s, 4H), 5.9~6.2(dd, 1H), 7.5~7.7(dd, 1H)

v) 5-(2,2,4,6,7-Pentamethylindan-5-yl)-cyclohexane-1,3-dione.

To a solution of 3.25 g of sodium in 100 ml of absolute methanol was added 23 ml of diethyl malonate, and then the reaction mixture was added 25.3 g of 4-(2,2,4,6,7-pentamethylindan-5-yl)-3-buten-2-one in 50 ml of absolute methanol. After refluxing for 4 hours, the reaction mixture was evaporated under reduced pressure and then added 100 g of 10% aqueous solution of NaOH. After refluxing for 4 hours, the reaction mixture was cooled to room temperature and washed twice with diethyl ether. Concentrated hydrochloric acid was added dropwise into the boiling aqueous layers until the bubble of gas ceased and then the reaction mixture was cooled to room temperature. Solid product was collected and dried to afford 23.8 g of the title compound as white solid. mp: 63~65° C.

¹H NMR(CDCl₃): δ 1.17(s, 6H), 2.21(s, 3H), 2.25(s, 3H), 2.28(s, 3H), 2.40~3.56(m, 7H), 5.30(s, 1H), 7.0(br, 1H)

vi) 5-(2,2,4,6,7-Pentamethylindan-5-yl)-2-propionyl-cyclohex-2-en-1-one.

To a solution of 14.7 g of the 5-(2,2,4,6,7-pentamethylindan-5-yl)-cyclohexane-1,3-dione in 100 ml of absolute toluene was added 25.6 ml of propionic anhydride. After refluxing for 4 hours, toluene and excess propionic anhydride were evaporated under reduced pressure to afford a residue. To the solution of the residue in 100 ml of toluene was added 1.22 g of dimethylaminopyridine and refluxed for 20 hours. The reaction mixture was evaporated under reduced pressure. The residue was purified by silica-gel column chromatography to afford 10.1 g of the title compound as yellow solid.

mp: 108~109° C.

¹H NMR(CDCl₃): δ 1.20(t, 3H), 1.20(s, 6H), 2.17(s, 3H), 2.25(s, 3H), 2.75(s, 3H), 2.50~3.40(m, 9H), 3.80~4.0(m, 1H), 10.8(br, 1H)

vii) 5-(2,2,4,6,7-Pentamethylindan-5-yl)-2-butyryl-cyclohex-2-en-1-one.

To a solution 14.7 g of the 5-(2,2,4,6,7-pentamethylindan-5-yl)-cyclohexane-1,3-dione in 100 ml of absolute toluene was added 32.7 ml of butyric anhydride. After refluxing for 4 hours, toluene and excess butyric anhydride were evaporated under reduced pressure to afford a residue. To the solution of the residue in 100 ml of toluene was added 1.22 g of dimethylaminopyridine and refluxed for 20 hours. The reaction mixture was evaporated under reduced pressure. The residue was purified by silica-gel column chromatography to afford 10.84 g of the title compound as yellow solid.

mp: 85~86° C.

¹H NMR(CDCl₃): δ 1.0(t, 3H), 1.15(s, 6H), 1.70(q, 2H), 2.10(s, 3H), 2.25(s, 3H), 2.30(s, 3H), 2.50~3.45(m, 10H), 3.80~4.0(s, 1H), 10.8(br, 1H)

viii) 5-(2,2,4,6,7-pentamethylindan-5-yl)-2-[1-(allyloxyimino)pyropyl]-3 -hydroxycyclohex-2-en-1-one To a solution 0.35 g of the 5-(2,2,4,6,7-pentamethylindan-5-yl)-2-propionyl-cyclohex-2-en-1-one in 10 ml of ethanol was added 0.16 g of sodium acetate (NaOAc.3H₂O) and 0.13 g of allyloxylamine. After stirring at room temperature for 10 hours, the reaction mixture extracted with diethyl ether. The combined organic layer was dried over anhydrous magnesium sulfate, filtered and evaporated under reduced pressure. The residue was purified by silica-gel column chromatography to afford 0.43 g of the title compound as yellow foam.

¹H NMR(CDCl₃): δ 1.20(t, 3H), 1.20(s, 6H), 2.17(s, 3H), 2.25(s, 3H), 2.75(s, 3H), 2.50~3.40(m, 10H), 3.80~4.0(m, 1H), 4.6(d, 2H), 5.5(dd, 2H), 5.8~6.2(m, 1H), 10.8(br, 1H)

EXAMPLE 2

5-(2-Ethyl-2,4,5,7-tetramethylindan-6-yl)-2-[1-(allyloxyimino)propyl]-3-hydroxycyclohex-2-en-1-one.

i) 2-Ethyl-2,4,5,7-tetramethylindan-1,3-dione.

To a mixture of 18.0 ml of 1,2,4-trimethylbenzene and 22.8 g of ethylmethylmalonyl chloride in 200 ml of dry dichloromethane was added slowly 32 g of AlCl₃ under the current of nitrogen gas at −10° C. The reaction mixture was stirred at room temperature for 2 hours, quenched with 200 g of ice, and separated the organic layer. The aqueous layer was extracted with dichloromethane. The combined organic layer was dried over anhydrous magnesium sulfate, filtered and evaporated under reduced pressure. The residue was purified by silica-gel column chromatography to afford 26 g of the title compound as a yellow solid.

Yield: 93% bp: 94~95° C./0.01 torr

¹H NMR(CDCl₃): δ 0.7(t, 3H), 1.20(s, 3H), 1.71(q, 2H), 2.44(s, 3H), 2.68(s, 6H), 7.3(s, 1H)

ii) 2-Ethyl-2,4,5,7-tetramethylindane

To a mixture of 60 g of 7% Zn/Hg in 200 ml of 20% hydrochloric acid and 70 ml of ethanol was added 27.92 g of the 2-ethyl-2,4,5,7-tetramethylindan-1,3-dione with stirring. After refluxing for 6 hours, the reaction mixture was added 100 ml of benzene and refluxed for 3 hour. The reaction mixture was cooled to room temperature and extracted with diethyl ether. The combined organic layer was dried over anhydrous magnesium sulfate, filtered and evaporated under reduced pressure. The residue was purified by silica-gel column chromatography to afford 17.77 g of the title compound as yellow oil.

Yield: 72.4%

¹H NMR(CDCl₃): δ 0.9(t, 3H), 1.05(s, 3H), 1.52(q, 2H), 2.11(s, 3H), 2.21(s, 6H), 2.92(s, 4H), 6.61(s, 1H)

iii) 2-Ethyl-2,4,5,7-tetramethylindan-6-carboxaldehyde

To a solution of 17.7 g of the 2-ethyl-2,4,5,7-tetramethylindane in 100 ml of dry dichloromethane was continuously added 9.5 ml of α,α-dichloromethyl methyl ether and 11.6 ml of TiCl₄ at 0° C. The reaction mixture was stirred at room temperature for 2 hours, quenched with 200 ml of water, and separated the organic layer. The aqueous layer was extracted with dichloromethane. The combined organic layer was dried over magnesium sulfate, filtered and evaporated under reduced pressure. The residue was purified by silica-gel column chromatography to afford 18.26 g of the title compound as brown solid.

yield: 90%

¹H NMR(CDCl₃): δ 0.9(t, 3H), 1.05(s, 3H), 1.52(q, 2H), 2.11(s, 3H), 2.20(s, 3H), 2.22(s, 3H), 2.85(s, 4H), 10.5(s, 1H)

iv) 4-(2-Ethyl-2,4,5,7-tetramethylindan-6-yl)-3-butene-2-one

To a solution of 18.26 g of the 2-ethyl-2,4,5,7-tetramethylindan-6-carboxaldehyde in 58 ml of absolute acetone was added 28 ml of water and 32 g of 2% NaOH. After refluxing for 20 hours, the solution was acidified was 2N HCl and extracted with diethyl ether. The organic layer was dried over anhydrous magnesium sulfate, filtered and evaporated under reduced pressure. The residue was purified by silica-gel column chromatography to afford 19.38 g of the title compound as yellow oil.

yield: 79%

¹H NMR(CDCl₃): δ 0.9(t, 3H), 1.05(s, 3H), 1.52(q, 2H), 2.10(s, 3H), 2.11(s, 3H), 2.20(s, 3H), 2.22(s, 3H), 2.85(s, 4H), 6.2(dd, 1H), 7.5~7.7(dd, 1H)

v) 5-(2-Ethyl-2,4,5,7-tetramethylindan-6-yl)-cyclohexane-1,3-dione.

To a solution of 2.47 g of sodium in 100 ml of absolute methanol was added 16.3 ml of diethyl malonate, and then the reaction mixture was added 19.38 g of 4-(2-ethyl-2,4,5,7-tetramethylindan-6-yl)-3-buten-2-one in 50 ml of absolute methanol. After refluxing for 4 hours, the reaction mixture was evaporated under reduced pressure and then added 115 g of 10% aqueous solution of NaOH. After refluxing for 4 hours, the reaction mixture was cooled to room temperature and washed twice with diethyl ether. Concentrated hydrochloric acid was added dropwise into the boiling aqueous layers until the bubble of gas ceased and then the reaction mixture was cooled with room temperature. Solid product was collected and dried to afford 22.0 g of the title compound.

Yield: 98.6%

$^1$H NMR(CDCl$_3$): δ 0.95(t, 3H), 1.05(s, 3H), 1.52(q, 2H), 2.20(s, 3H), 2.30(s, 3H), 2.32(s, 3H), 2.40~3.36(m, 7H), 5.30(s, 1H), 9.5(br, 1H)

vi) 5-(2-Ethyl-2,4,5,7-tetramethylindan-6-yl)-2-propionyl-cyclohex-2-en-1-one.

To a solution of 7.8 g of the 5(2-ethyl-2,4,5,7-pentamethylindan-6-yl)-cyclohexane-1,3-dione in 70 ml of absolute toluene was added 12.8 ml of propionic anhydride. After refluxing for 4 hours, toluene and excess propionic anhydride were evaporated under reduced pressure to afford a residue. To the solution of the residue in 100 ml of toluene was added 0.61 g of dimethylaminopyridine and refluxed for 20 hours. The reaction mixture was evaporated under reduced pressure. The residue was purified by silica-gel column chromatography to afford 4.19 g of the title compound as yellow solid Yield: 45.5%

$^1$H NMR(CDCl$_3$): δ 0.9(t, 3H), 1.10(s, 3H), 1.18(t, 3H), 1.52(q, 2H), 2.17(s, 3H), 2.25(s, 3H), 2.30(s, 3H), 2.52~2.50 (m, 6H), 3.05~3.47(m, 4H), 3.80~4.05(m, 1H), 11.2(br, 1H)

vii) 5-(2-Ethyl-2,4,5,7-tetramethylindan-6-yl)-2-butyryl-cyclohex-2-en-1-one.

To a solution 7.8 g of the 5-(2-ethyl-2,4,5,7-tetramethylindan-6-yl)-cyclohexane-1,3-dione in 100 ml of absolute toluene was added 16.4 ml of butyric anhydride. After refluxing for 4 hours, toluene and excess butyric anhydride were evaporated under reduced pressure to afford a residue. To the solution of the residue in 100 ml of toluene was added 0.61 g of dimethylaminopyridine and refluxed for 20 hours. The reaction mixture was evaporated under reduced pressure. The residue was purified by silica-gel column chromatography to afford 44.43 g of the title compound as yellow solid.

Yield: 46.3% mp: 69~71° C.

$^1$H NMR(CDCl$_3$): δ 0.90(t, 3H), 1.10(s, 3H), 1.18(t, 3H), 1.52(q, 2H), 1.67(m, 2H), 2.17(s, 3H), 2.25(s, 3H), 2.30(s, 3H), 2.52~2.50(m, 6H), 3.05~3.47(m, 4H), 3.80~4.05(m, 1H), 11.2(br, 1H)

viii) 5-(2-Ethyl-2,4,5,7-tetramethylindan-6-yl)-2-[1-(allyloxyimino)propyl]-3-hydroxycyclohex-2-en-1-one To a solution 0.37 g of the 5-(2-ethyl-2,4,5,7-tetramethylindan-6-yl)-2-propionyl-cyclohex-2-end-1-one in 10 ml of ethanol was added 0.16 g of sodium acetate (NaOAc.3H$_2$O) and 0.13 g of allyloxylamine hydrochloride. After stirring at room temperature for 10 hours, the reaction mixture extracted with diethyl ether. The combined organic layer was dried over anhydrous magnesium sulfate, filtered and evaporated under reduced pressure. The residue was purified by silica-gel column chromatography to afford 0.35 g of the title compound as yellow solid.

mp: 64~65° C.

$^1$H NMR(CDCl$_3$): δ 0.90(t, 3H), 1.10(s, 3H), 1.18(t, 3H), 1.52(q, 2H), 2.17 (s, 3H), 2.25(s, 3H), 2.30(s, 3H), 2.52~2.50(m, 6H), 3.05~3.47(m, 4H), 3.80~4.05(m, 1H), 4.5(d, 2H), 5.15~5.50(m, 2H), 5.6~6.2(m, 1H), 11.2(br, 1H)

EXAMPLE 3

5-(6-Chloro-2,2,4,7-tetramethylindan-5-yl)-2-[1-(ethoxyimino)butyl]-3-hydroxycyclohex-2-en-1-one.

i) 6-Chloro-2,2,4,7-tetramethylindan-1,3-dione.

To a mixture of 30 ml of 2-chloro-p-xylene and 24.38 g of dimethylmalonyl chloride in 150 ml of dry dichloromethane was added slowly 38 g of AlCl$_3$ under the current of nitrogen gas at −10° C. The reaction mixture was stirred at room temperature of 2 hours, quenched with 200 g of ice, and separated the organic layer. The aqueous layer was extracted with dichloromethane. The combined organic layer was dried over anhydrous magnesium sulfate, filtered and evaporated under reduced pressure. The residue was purified by silica-gel column chromatography to afford 27.4 g of the title compound as a yellow solid.

Yield: 79.6%

$^1$H NMR(CDCl$_3$): δ 1.3(s, 6H), 2.40(s, 3H), 2.7(s, 3H), 7.62(s, 1H)

ii) 6-Chloro-2,2,4,7-tetramethylindane

To a mixture of 100 g of 7% Zn/Hg in 200 ml of 20% hydrochloric acid and 70ml of ethanol was added 27.32 g of the 6-chloro-2,2,4,7-tetramethylindan-1,3-dione with stirring. After refluxing for 6 hours, the reaction mixture was added 100 ml of benzene and refluxed for 1 hour. The reaction mixture was cooled to room temperature and extracted with diethyl ether. The combined organic layer was dried over anhydrous magnesium sulfate, filtered and evaporated under reduced pressure. The residue was purified by silica-gel column chromatography to afford 15.67 g of the title compound as yellow oil.

Yield: 81%

$^1$H NMR(CDCl$_3$): δ 1.20(s,6H), 2.10(s, 3H), 2.25(s, 3H), 2.65(s, 4H), 6.90(s, 1H)

iii) 6-Chloro-2,2,4,7-tetramethylindan-5-carboxaldehyde

To a solution of 19.8 g of the 6-chloro-2,2,4,7-tetramethylindane in 100 ml of dry dichloromethane was continuously added 13 ml of α,α-dichloromethyl methyl ether and 12.4 ml of TiCl$_4$ at 0° C. The reaction mixture was stirred at room temperature for 2 hours, quenched with 200 ml of water, and separated the organic layer. The aqueous layer was extracted with dichloromethane. The combined organic layer was dried over magnesium sulfate, filtered and evaporated under reduced pressure. The residue was purified by silica-gel column chromatography to afford 21.8 g of the title compound as yellow solid.

yield: 83.3% mp: 127° C.

$^1$H NMR(CDCl$_3$): δ 1.20(s, 6H), 2.3(s, 3H), 2.35(s, 3H), 2.36(s, 3H), 2.75(s, 4H), 10.8(s, 1H)

iv) 4-(6-Chloro-2,2,4,7-tetramethylindan-5-yl)-3-buten-2-one

To a solution of 21.8 g of the 6-chloro-2,2,4,7-tetramethylindan-5-carboxaldehyde in 67 ml of absolute acetone was added 33 ml of water and 36.5 g of 2% NaOH. After refluxing for 20 hours, the solution was acidified with 2N HCl and extracted with diethyl ether. The organic layer was dried over anhydrous magnesium sulfate, filtered and evaporated under reduced pressure. The residue was purified by silica-gel column chromatography to afford 16.6 g of the title compound as yellow solid.

yield: 65%

$^1$H NMR(CDCl$_3$): δ 1.20(s, 6H), 2.20(s, 3H), 2.30(s, 6H), 2.35(s, 3H), 2.70(s, 4H). 6.1~6.3(dd, 1H), 7.45~7.60(dd, 1H)

v) 5-(6-Chloro-2,2,4,7-tetramethylindan-5-yl)-cyclohexane-1,3-dione.

To a solution of 1.9 g of sodium in 100 ml of absolute methanol was added 14 ml of diethyl malonate, and then the reaction mixture was added 16.6 g of 4-(6-chloro-2,2,4,7-tetramethylindan-5-yl)-3-buten-2-one in 50 ml of absolute methanol. After refluxing for 4 hours, the reaction mixture was evaporated under reduced pressure and then added 100 g of 10% aqueous solution of NaOH. After refluxing for 4 hours, the reaction mixture was cooled to room temperature and washed twice with diethyl ether. Concentrated hydrochloric acid was added dropwise into the boiling aqueous layers until the bubble of gas ceased and then the reaction mixture was cooled to room temperature. Solid product was collected and dried to afford 19 g of the titile compound as yellow solid.

mp: 129~139° C.

$^1$H NMR(CDCl$_3$): δ 1.15(s, 6H), 2.21(s, 3H), 2.23(s, 3H), 2.7(s, 4H), 240~3.56(m, 9H), 5.30(s, 1H), 7.8(br, 1H)

vi) 5-(Chloro-2,2,4,7-tetramethylindan-5-yl)-2-propionyl-cyclohex-2-en-1-one.

To a solution of 8.02 g of the 5-(6-chloro-2,2,4,7-tetramethylindan-5-yl)-cyclohexane-1,3-dione in 100 ml of absolute toluene was added 12.8 ml of propionic anhydride. After refluxing for 4 hours, toluene and excess propionicanhydride were evaporated under reduced pressure to afford a residue. To the solution of the residue in 100 ml of toluene was added 0.61 g of dimethylaminopyridine and refluxed for 20 hours. The reaction mixture was evaporated under reduced pressure. The residue was purified by silica-gel column chromatography to afford 10.1 g of the title compound as yellow solid.

mp: 125~127° C.

$^1$H NMR(CDCl$_3$): δ 1.15(t, 3H), 1.15(s, 6H), 2.10(s, 3H), 2.12(s, 3H), 2.50~3.40(m, 10H), 3.80~4.0(m, 1H), 10.8(br, 1H)

vii) 5-(6-Chloro-2,2,4,7-tetramethylindan-5-yl)-2-butyryl-cyclohex-2-en-1-one.

To a solution 8.02 g of the 5-(6-chloro-2,2,4,7-tetramethylindan-5-yl)-cyclohexane-1,3-dione in 100 ml of absolute toluene was added 13.4 ml of butyric anhydride. After refluxing for 4 hours, toluene and excess butyric anhydride were evaporated under reduced pressure to afford a residue. To the solution of the residue in 100 ml of toluene was added 0.61 g of dimethylaminopyridine and refluxed for 20 hours. The reaction mixture was evaporated under reduced pressure. The residue was purified by silica-gel column chromatography to afford 3.51 g of the title compound as yellow solid.

Yield: 36% mp: 93~94° C.

$^1$H NMR(CDCl$_3$): δ 1.0(t, 3H), 1.15(s, 6H), 1.68(q, 2H), 2.12(s, 3H), 2.21(s, 3H), 2.50~3.45(m, 10H), 3.80~4.0(s, 1H), 10.8(br, 1H)

vii) 5-(6-Chloro-2,2,4,7-tetramethylindan-5-yl)-2-[1-(ethoxyimino)butyl]-3-hydroxycyclohex-2-en-1-one To a solution 0.39 g of the 5-(6-chloro-2,2,4,7-tetramethylindan-5-yl)-2-propionyl-cyclohex-2-en-1-one in 10 ml of ethanol was added 0.16 g of sodium acetate (NaOAc.3H$_2$O) and 0.13 g of ethoxylamine. After stirring at room temperature for 10 hours, the reaction mixture extracted with diethyl ether. The combined organic layer was dried over anhydrous magnesium sulfate, filtered and evaporated under reduced pressure. The residue was purified by silica-gel column chromatography to afford 0.553 g of the title compound as yellow foam.

$^1$H NMR(CDCl$_3$): δ 1.0(t, 3H), 1.15(s, 6H), 1.32(t, 3H), 1.68(q, 2H), 2.12(s, 3H), 2.21(s, 3H), 2.50~3.45(m, 10H), 3.80(s, 3H), 4.0(q, 2H), 10.8(br, 1H)

EXAMPLE 4

5-(6-Chloro-2-ethyl-2,4,7-trimethylindan-5-yl)-2-[1-(ethoxyimino)propyl]-3-hydroxycyclohex-2-en-1-one.

i) 6-Chloro-2-ethyl-2,4,7-trimethylindan-5-yl-1,3-dione.

To a mixture of 24 ml of 4-chloro-p-xylene and 31.3 g of ethylmethylmalonyl chloride in 250 ml of dry dichloromethane was added slowly 34.4 g of AlCl$_3$ under the current of nitrogen gas at 0° C. The reaction mixture was stirred at room temperature for 2 hours, quenched with 200 g of ice, and separated the organic layer. The aqueous layer was extracted with dichloromethane. The combined organic layer was dried over anhydrous magnesium sulfate, filtered and evaporated under reduced pressure. The residue was purified by silica-gel column chromatography to afford 33.1 g of the title compound as a yellow solid.

Yield: 81.6% mp: 95~96° C.

$^1$H NMR(CDCl$_3$): δ 0.8(t, 3H), 1.2(s, 3H), 1.8(q, 2H), 2.75(s, 3H), 2.83(s, 3H), 7.62(s, 1H)

ii) 6-Chloro-2-ethyl-2,4,7-trimethylindane

To a mixture of 83 g of 7% Zn/Hg in 70 ml of 20% hydrochloric acid and 70 ml of ethanol was added 40.0 g of the 6-chloro-2-ethyl-2,4,7-trimethylindan-5-yl-1,3-dione with stirring. After refluxing for 6 hours, the reaction mixture was added 100 ml of benzene and refluxed for 1 hour. The reaction mixture was cooled to room temperature and extracted with diethyl ether. The combined organic layer was dried over anhydrous magnesium sulfate, filtered and evaporated under reduced pressure. The residue was purified by silica-gel column chromatography to afford 19.4 g of the title compound as yellow oil.

Yield: 52.5%

$^1$H NMR(CDCl$_3$): δ 0.9(t, 3H), 1.05(s, 3H), 1.5(t, 2H), 2.21(s, 3H), 2.27(s, 3H), 2.6(s, 4H), 7.62(s, 1H)

iii) 6-Chloro-2-ethyl-2,4,7-trimethylindan-5-carboxaldehyde

To a solution of 19 g of the 6-chloro-2-ethyl-2,4,7-trimethylindane in 100 ml of dry dichloromethane was continuously added 9.5 ml of α,α-dichloromethyl methyl ether and 11.5 ml of TiCl$_4$ at 0° C. The reaction mixture was stirred at room temperature for 2 hours, quenched with 100 ml of water, and separated the organic layer. The aqueous layer was extracted with dichloromethane. The combined organic layer was dried over magnesium sulfate, filtered and evaporated under reduced pressure. The residue was purified by silica-gel column chromatography to afford 20.85 g of the title compound as yellow solid.

yield: 97% mp: 89~90° C.

$^1$H NMR(CDCl$_3$): δ 0.9(t, 3H), 1.05(s, 3H), 1.5(q, 2H), 2.21(s, 3H), 2.45(s, 3H), 2.8(s, 4H), 10.65(s, 1H).

iv) 4-(6-Chloro-2-ethyl-2,4,7-trimethylindan-5-yl)-3-buten-2-one

To a solution of 24.35 g of the 6-chloro-2-ethyl-2,4,7-trimethylindan-5-carboxaldehyde in 73 ml of absolute acetone was added 36 ml of water and 40 g of 2% NaOH. After refluxing for 20 hours, the solution was acidified with 2N HCl and extracted with diethyl ether. The organic layer was dried over anhydrous magnesium sulfate, filtered and evaporated under reduced pressure. The residue was purified by silica-gel column chromatography to afford 22.08 g of the title compound as brown oil.

yield: 78%

$^1$H NMR(CDCl$_3$): δ 0.9(t, 3H), 1.05(s, 3H), 1.5(q, 2H), 2.10(s, 3H), 2.21(s, 3H), 2.35(s, 3H), 2.8(s, 4H), 6.1~6.3(dd, 1H), 7.45~7.60(dd, 1H)

v) 5-(6-Chloro-2-ethyl-2,4,7-trimethylindan-5-yl)-cyclohexane-1,3-dione.

To a solution of 2.7 g of sodium in 100 ml of absolute methanol was added 100 ml of diethyl malonate, and then the reaction mixture was added 22.08 g of 4-(6-chloro-2-ethyl-2,4,7-trimethylindan-5-yl)-3-buten-2-one in 50 ml of absolute methanol. After refluxing for 4 hours, the reaction mixture was evaporated under reduced pressure and then added 12.3 g of 10% aqueous solution of NaOH. After refluxing for 4 hours, the reaction mixture was cooled to room temperature and washed twice with diethyl ether. Concentrated hydrochloric acid was added dropwise into the boiling aqueous layers until the bubble of gas ceased and then the reaction mixture was cooled to room temperature. Solid product was collected and dried to afford 23 g of the titile compound as yellow solid.

mp: 79~80° C.

$^1$H NMR(CDCl$_3$): δ 0.9(t, 3H), 1.05(s, 3H), 1.5(q, 2H), 2.20(s, 3H), 2.21(s, 3H), 2.40~2.85(m, 9H), 3.5~4.1(m, 1H), 5.30(s, 1H), 9.5(br, 1H).

vi) 5-(6-Chloro-2-ethyl-2,4,7-trimethylindan-5-yl)-2-propionyl-cyclohex-2-en-1-one.

To a solution of 9.3 g of the 5-(6-chloro-2-ethyl-2,4,7-trimethylindan-5-yl)-cyclohexane-1,3-dione in 50 ml of absolute toluene was added 15 ml of propionic anhydride. After refluxing for 4 hours, toluene and excess propionic anhydride were evaporated under reduced pressure to afford a residue. To the solution of the residue in 50 ml of toluene was added 0.6 g of dimethylaminopyridine and refluxed for 20 hours. The reaction mixture was evaporated under reduced pressure. The residue was purified by silica-gel column chromatography to afford 4.96 g of the title compound as yellow solid.

$^1$H NMR(CDCl$_3$): δ 0.9(t, 3H), 1.05(s, 3H), 1.15(t, 3H), 1.5(q, 2H), 2.20(s, 3H), 2.21(s, 3H), 2.40~2.85(m, 11H), 3.5~4.1(m, 1H), 5.30(s, 1H), 9.5(br, 1H).

vii) 5-(6-Chloro-2-ethyl-2,4,7-trimethylindan-5-yl)-2-buryryl-cyclohex-2-en-1-one.

To a solution 9.3 g of the 5-(6-chloro-2-ethyl-2,4,7-trimethylindan-5-yl)-cyclohexane-1,3-dione in 50 ml of absolute toluene was added 19 ml of buryric anhydride. After refluxing for 4 hours, toluene and excess butyric anhydride were evaporated under reduced pressure to afford a residue. To the solution of the residue in 100 ml of toluene was added 0.6 g of dimethylaminopyridine and refluxed for 20 hours. The reaction mixture was evaporated under reduced pressure. The residue was purified by silica-gel column chromatography to afford 4.10 g of the title compound as yellow solid.

Yield: 36% mp: 56~58° C.

$^1$H NMR(CDCl$_3$): δ 1.0(t, 3H), 1.15(s, 6H), 1.52(t, 3H), 1.68(m, 2H), 2.120(s, 3H), 2.21(s, 3H), 2.50~3.45(m, 10H), 3.80~4.0(s, 1H), 10.8(br, 1H)

viii) 5-(6-Chloro-2-ethyl-2,4,7-trimethylindan-5-yl)-2-[1-(ethoxyimino)propyl]-3-hydroxycyclohex-2-en-1-one To a solution 0.15 g of the 5-(6-chloro-2-ethyl-2,4,7-trimethylindan-5-yl)-2-propionyl-cyclohex-2-en-1-one in 10 ml of ethanol was added 0.9 g of sodium acetate (NaOAc.3H$_2$O) and 0.64 g of ethoxylamine hydrochloride. After stirring at room temperature for 10 hours, the reaction mixture extracted with diethyl ether. The combined organic layer was dried over anhydrous magnesium sulfate, filtered and evaporated under reduced pressure. The residue was purified by silica-gel column chromatography to afford 0.1153 g of the title compound as yellow oil.

$^1$H NMR(CDCl$_3$): δ 0.9(t, 3H), 1.05(s, 3H), 1.12(t, 3H), 1.15(t, 3H), 1.5(q, 2H), 2.20(s, 3H), 2.21(s, 3H), 2.40~2.85 (m, 11H), 3.5~4.0(m, 1H), 4.15(q, 2H), 5.30(s, 1H), 9.5(br, 1H).

EXAMPLE 5

5-(7-Chloro-2,2,4,5-tetramethylindan-6-yl)-2-[1-(ethoxyimino)butyl]-3-hydroxycyclohex-2-en-1-one.

i) 7-Chloro-2,2,4,5-tetramethylindan-1,3-dione

To a mixture of 35.5 ml of 4-chloro-o-xylene and 29.84 g of dimethylmalonyl chloride in 150 ml of dry dichloromethane was added slowly 34.7 g of AlCl$_3$ under the current of nitrogen gas at −10° C. The reaction mixture was stirred at room temperature for 2 hours, quenched with 200 g of ice, and separated the organic layer. The aqueous layer was extracted with dichloromethane. The combined organic layer was dried over anhydrous magnesium sulfate, filtered and evaporated under reduced pressure. The residue was purified by silica-gel column chromatography to afford 34.99 g of the title compound as yellow solid.

Yield: 83%

$^1$H NMR(CDCl$_3$): δ 1.26(s, 6H), 2.45(s, 3H), 2.65(s, 3H), 7.50(s, 1H)

ii) 7-Chloro-2,2,4,5-tetramethylindane

To a mixture of 100 g of 7% Zn/Hg in 200 ml of 20% hydrochloric acid and 70 ml of ethanol was added 38.42 g of the 7-chloro-2,2,4,5-tetramethylindan-1,3-dione with stirring. After refluxing for 6 hours, the reaction mixture was added 100 ml of benzene and refluxed for 1 hour. The reaction mixture was cooled to room temperature and extracted with diethyl ether. The combined organic layer was dried over anhydrous magnesium sulfate, filtered and evaporated under reduced pressure. The residue was purified by silica-gel column chromatography to afford 17.0 g of the title compound as yellow oil.

Yield: 50%

$^1$H NMR(CDCl$_3$): δ 1.20(s, 6H), 2.10(s, 3H), 2.20(s, 3H), 2.70(dd, 4H), 6.90(s, 1H)

iii) 7-Chloro-2,2,4,5-tetramethylindan-6-carboxaldehyde

To a solution of 17.0 g of the 7-chloro-2,2,4,5-tetramethylindane in 100 ml of dry dichloromethane was continuously added 18.5 ml of α,α-dichloromethyl methyl ether and 11 ml of TiCl$_2$ at 0° C. The reaction mixture was stirred at room temperature for 2 hours, quenched with 200 ml of water, and separated the organic layer. The aqueous layer was extracted with dichloromethane. The combined organic layer was dried over magnesium sulfate, filtered and evaporated under reduced pressure. The residue was purified by silica-gel column chromatography to afford 14.7 g of the title compound as yellow solid.

yield: 76.6% mp: 108° C.

$^1$H NMR(CDCl$_3$): δ 1.30(s, 6H), 2.20(s, 3H), 2.45(s, 3H), 2.35(s, 3H), 2.85(s, 4H), 10.8(s, 1H)

iv) 4-(7-Chloro-2,2,4,5-tetramethylindan-6-yl)-3-buten-2-one

To a solution of 14.7 g of the 7-chloro-2,2,4,5-tetramethylindan-6-carboxaldehyde in 48 ml of absolute acetone was added 23 ml of water and 25 g of 2% NaOH. After refluxing for 20 hours the solution was acidified with 2N HCl extracted with diethyl ether. The organic layer was dried over anhydrous magnesium sulfate, filtered and evaporated under reduced pressure. The residue was purified by silica-gel column chromatography to afford 5.35 g of the title compound as yellow solid.

yield: 35%

$^1$H NMR(CDCl$_3$): δ 1.20(s, 6H), 2.15(s, 3H), 2.26(s, 6H), 2.30(s, 3H), 2.80(s, 4H), 615~6.4(dd, 1H), 7.45~7.70(dd, 1H)

v) 5-(7-Chloro-2,2,4,5-tetramethylindan-6-yl)-cyclohexane-1,3-dione

To a solution of 1.3 g of sodium in 50 ml of absolute methanol was added 8 ml of diethyl malonate, and then the reaction mixture was added 9.41 g of 5-(5-chloro-2,2,4,7-tetramethylindan-6-yl)-3-buten-2-one in 50 ml of absolute methanol. After refluxing for 4 hours, the reaction mixture was evaporated under reduced pressure and then added 100 g of 10% aqueous solution of NaOH. After refluxing for 4 hours, the reaction mixture was cooled to room temperature and washed twice with diethyl ether. Concentrated hydrochloric acid was added dropwise into the boiling aqueous layers until the bubble of gas ceased and then the reaction mixture was cooled to room temperature. Solid product was collected and dried to afford 9.24 g of the titile compound as white solid.

Yield: 77%

$^1$H NMR(CDCl$_3$): δ 1.15(s, 6H), 2.21(s, 3H), 2.23(s, 3H), 2.7(s, 4H), 240~356(m, 9H), 5.30(s, 1H), 7.8(br, 1H)

vi) 5-(7-Chloro-2,2,4,5-tetramethylindan-6-yl)-2-propionyl-cyclohex-2-en-1-one

To a solution of 4.52 g of the 5-(7-chloro-2,2,45-tetramethylindan-6-yl)-cyclohexane-1,3-dione in 70 ml of absolute toluene was added 7.2 ml of propionic anhydride. After refluxing for 4 hours, toluene and excess propionic anhydride were evaporated under reduced pressure to afford a residue. To the solution of the residue in 100 ml of toluene was added 0.35 g of dimethylaminopyridine and refluxed for 20 hours. The reaction mixture was evaporated under reduced pressure. The residue was purified by silica-gel column chromatography to afford 2.13 g of the title compound as yellow solid.

mp: 74~75° C.

$^1$H NMR(CDCl$_3$): δ 1.15(t, 3H), 1.15(s, 6H), 2.10(s, 3H), 2.12(s, 3H), 250~3.40(m, 10H), 3.80~4.0(m, 1H), 10.8(br, 1H)

vii) 5-(7-Chloro-2,2,4,5-tetramethylindan-6-yl)-2-butyryl-cyclohex-2-en-1-one

To a solution 4.62 g of the 5-(7-chloro-2,2,4,5-tetramethylindan-6-yl)-cyclohexane-1,3-dione in 100 ml of absolute toluene was added 9.4 ml of butyric anhydride. After refluxing for 4 hours, toluene and excess butyric anhydride were evaporated under reduced pressure to afford a residue. To the solution of the residue in 100 ml of toluene was added 0.35 g of dimethylaminopyridine and refluxed for 20 hours. The reaction mixture was evaporated under reduced pressure. The residue was purified by silica-gel column chromatography to afford 2.15 g of the title compound as yellow solid.

Yield: 38%

$^1$H NMR(CDCl$_3$): δ 1.0(t, 3H), 1.15(s, 6H), 1.68(q, 2H), 2.120(s, 3H), 2.21(s, 3H), 2.50~3.45(m, 10H), 3.80~4.0(s, 1H), 10.8(br, 1H)

viii) 5-(7-Chloro-2,2,4,5-tetramethylindan-6-yl)-2-[1-(ethoxyimino)butyl]-3-hydroxycyclohex-2-en-1-one To a solution 0.39 g of the 5-(7-chloro-2,2,4,5-tetramethylindan-6-yl)-2-propionyl-cyclohex-2-en-1-one in 10 ml of ethanol was added 0.16 g of sodium acetate (NaOAc.3H$_2$O) and 0.13 g of ethoxylamine hydrochloride. After stirring at room temperature for 10 hours, the reaction mixture extracted with diethyl ether. The combined organic layer was dried over anhydrous magnesium sulfate, filtered ande vaporated under reduced pressure. The residue was purified by silica-gel column chromatography to afford 0.29 g of the title compound as yellow foam.

$^1$H NMR(CDCl$_3$): δ 1.0(t, 3H), 1.15(s, 6H), 1.32(t, 3H), 1.68(q, 2H), 2.120(s, 3H), 2.21(s, 3H), 2.50~3.45(m, 10H), 3.80(s, 1H), 4.0(q, 2H), 10.8(br, 1H)

EXAMPLE 6

5-(7-Chloro-2-ethyl-2,4,5-trimethylindan-6-yl)-2-[1-(ethoxyimino)propyl]-3 hydroxycyclohex-2-en-1-one.

i) 7-Chloro-2-ethyl-2,4,5-trimethylindan-1,3-dione

To a mixture of 28 ml of 4-chloro-o-xylene and 37.6 g of ethylmethylmalonyl chloride in 300 ml of dry dichloromethane was added slowly 26.7 g of AlCl$_3$ under the current of nitrogen gas at −10° C. The reaction mixture was stirred at room temperature for 2 hours, quenched with 200 g of ice, and separated the organic layer. The aqueous layer was extracted with dichloromethane. The combined organic layer was dried over anhydrous magnesium sulfate, filtered and evaporated under reduced pressure. The residue was purified by silica-gel column chromatography to afford 24.67 g of the title compound as a yellow solid.

Yield: 50% mp: 97° C.

$^1$H NMR(CDCl$_3$): δ 0.7(t, 3H), 1.27(s, 3H), 1.80(t, 2H), 2.46(s, 3H), 2.70(s, 3H), 7.80(s, 1H)

ii) 7-Chloro-2-ethyl-2,4,5-trimethylindane

To a mixture of 66 g of 7% Zn/Hg in 70 ml of concentrated hydrochloric acid and 70 ml of ethanol was added 24.67 g of the 7-chloro-2-ethyl-2,4,5-trimethylindan-13-dione with stirring. After refluxing for 6 hours, the reaction mixture was added 100 ml of benzene and refluxed for 1 hour. The reaction mixture was cooled to room temperature and extracted with diethyl ether. The combined organic layer was dried over anhydrous magnesium sulfate, filtered and evaporated under reduced pressure. The residue was purified by silica-gel column chromatography to afford 9.23 g of the title compound as yellow oil.

Yield: 42%

$^1$H NMR(CDCl$_3$): δ 0.9(t, 3H), 1.12(s, 3H), 1.45(t, 2H), 2.05(s, 3H), 2.26(s, 3H), 2.7(s, 4H), 6.80(s, 1H)

iii) 7-Chloro-2-ethyl-2,4,5,-trimethylindan-6-carboxaldehyde

To a solution of 9.98 g of the 7-chloro-2-ethyl-2,4,5-trimethylindane in 100 ml of dry dichloromethane was continuously added 6.2 ml of α,α-dichloromethyl methyl ether and 7.5 ml of TiCl$_4$ at 0° C. The reaction mixture was stirred at room temperature for 2 hours, quenched with 100 ml of water, and separated the organic layer. The aqueous layer was extracted with dichloromethane. The combined organic layer was dried over magnesium sulfate, filtered and evaporated under reduced pressure. The residue was purified by silica-gel column chromatography to afford 9.23 g of the title compound as yellow solid.

yield: 82%

$^1$H NMR(CDCl$_3$): δ 0.9(t, 3H), 1.12(s, 3H), 1.45(t, 2H), 2.05(s, 3H), 2.26(s, 3H), 2.7(s, 4H), 10.80(s, 1H)

iv) 4-(7-Chloro-2-ethyl-2,4,5-trimethylindan-6-yl)-3-buten-2-one

To a solution of 14.7 g of the 7-chloro-2-ethyl-2,4,5-trimethylindan-6-carboxaldehyde in 45 ml of absolute acetone was added 22 ml of water and 24 g of 2% NaOH. After refluxing for 20 hours, the solution was acidified with 2N HCl and extracted with diethyl ether. The organic layer was dried over anhydrous magnesium sulfate, filtered and evaporated under reduced pressure. The residue was purified by silica-gel column chromatography to afford 12.65 g of the title compound as brown oil.

yield: 73.7%

$^1$H NMR(CDCl$_3$): δ 0.9(t, 3H), 1.12(s, 3H), 1.45(t, 2H), 2.05(s, 3H), 2.10(s, 3H), 2.26(s, 3H), 2.7(s, 4H), 615~6.4 (dd, 1H), 7.45~7.70(dd, 1H)

v) 5-(7-Chloro-2-ethyl-2,4,5-trimethylindan-6-yl)-cyclohexane-1,3-dione

To a solution of 1.53 g of sodium in 100 ml of absolute methanol was added 10 ml of diethyl malonate, and then the reaction mixture was added 12.65 g of 4-(5-chloro-2,2,4,7- tetramethylindan-6-yl)-3-buten-2-one in 50 ml of absolute methanol. After refluxing for 4 hours, the reaction mixture was evaporated under reduced pressure and then added 70 g of 10% aqueous solution of NaOH. After refluxing for 4 hours, the reaction mixture was cooled to room temperature and washed twice with diethyl ether. Concentrated hydrochloric acid was added dropwise into the boiling aqueous layers until the bubble of gas ceased and then the reaction mixture was cooled to room temperature. Solid produce was collected and dried to afford 11.9 g of the titile compound as yellow solid.

Yield: 87%

$^1$H NMR(CDCl$_3$): δ 0.95(t, 3H), 1.0(s, 3H), 1.5(t, 2H), 2.10(s, 3H), 2.26(s, 3H), 2.40~3.56(m, 9H), 5.30(s, 1H), 10.5(br, 1H).

vi) 5-(7-Chloro-2-ethyl-2,4,5-trimethylindan-6-yl)-2-propionyl-cyclohex-2-en-1-one To a solution of 7.12 g of the 5-(7-chloro-2-ethyl-2,4,5-trimethylindan-6-yl)-cyclohexane-1,3-dione in 70 ml of absolute toluene was added 11.8 ml of propionic anhydride. After refluxing for 4 hours, toluene and excess propionic anhydride were evaporated under reduced pressure to afford a residue. To the solution of the residue in 100 ml of toluene was added 0.56 g of dimethylaminopyridine and refluxed for 20 hours. The reaction mixture was evaporated under reduced pressure. The residue was purified by silica-gel column chromatography to afford 4.53 g of the title compound as yellow solid.

Yield: 54% mp: 55~57° C.

$^1$H NMR(CDCl$_3$): δ 0.9(t, 3H), 1.07(s, 3H), 1.15(t, 3H), 1.50(t, 2H), 2.15(s, 3H), 2.25(s, 3H), 2.40~2.87(m, 9H), 3.08(q, 2H), 5.30(s, 1H), 10.5(br, 1H).

vii) 5-(7-Chloro-2-ethyl-2,4,5-trimethylindan-6-yl)-2-butyryl-cyclohex-2-en-1-one To a solution 7.12 g of the 5-(7-chloro-2-ethyl-2,4,5-trimethylindan-6-yl)-cyclohexane-1,3-dione in 70 ml of absolute toluene was added 15 ml of buryric anhydride. After refluxing for 4 hours, toluene and excess butyric anhydride were evaporated under reduced pressure to afford a residue. To the solution of the residue in 100 ml of toluene was added 0.56 g of dimethylaminopyridine and refluxed for 20 hours. The reaction mixture was evaporated under reduced pressure. The residue was purified by silica-gel column chromatography to afford 4.64 g of the title compound as yellow solid.

Yield: 53% mp: 45~47

$^1$H NMR(CDCl$_3$): δ 0.9(t, 3H), 1.07(s, 3H), 1.15(t, 3H), 1.50(t, 2H), 1.68(m, 2H), 2.15(s, 3H), 2.25(s, 3H), 2.40~2.87(m, 9H), 3.08(q, 2H), 5.30(s, 1H), 10.5(br, 1H).

viii) 5-(7-Chloro-2-ethyl-2,4,5-trimethylindan-6-yl)-2-[1-(ethoxyimino)propyl]-3-hydroxycyclohex-2-en-1-one To a solution 0.37 g of the 5-(7-chloro-2-ethyl-2,4,5-trimethylindan-6-yl)-2-propionyl-cyclohex-2-en-1-one in 10 ml of ethanol was added 0.16 g of sodium acetate (NaOAc.3H$_2$O) and 0.13 g of ethoxylamine hydrochloride. After stirring at room temperature for 10 hours, the reaction mixture extracted with diethyl ether. The combined organic layer was dried over anhydrous magnesium sulfate, filtered and evaporated under reduced pressure. The residue was purified by silica-gel column chromatography to afford 0.338 g of the title compound as yellow solid.

mp: 93~94° C.

$^1$H NMR(CDCl$_3$): δ 0.9(t, 3H), 1.07(s, 3H), 1.15(t, 3H), 1.22(t, 3H), 1.50(t, 2H), 2.15(s, 3H), 2.25(s, 3H), 2.40~2.87 (m, 9H), 3.08(q, 2H), 4.0(q, 2H), 10.5(br, 1H).

Novel cyclohexane-1,3-dione derivatives of the formula (1) according to the present invention are sufficiently tolerant on most broad leaved plant such as soybeans, cotton, sunflower, sugarbeet and various kings of vegetables and may be available for post-emergent control of grassy weeds in said crops.

The compounds of formula(1) according to the present invention may be applied for instance in form of wettable powders, dust, flowable concentrates, granules, solutions or emulsifiable concentrates.

The content of the compound of the formula(1) is usually from 0.1 to 95% by weight for these formulations in order to get sufficient effects as herbicides and plant-growth regulants.

To prepare the above formulations it can be used either solid carrier or liquid carrier. As solid carriers, inorganic powders such as kaolinite, bentonite, montmorillonite, talc diatomaceous earth, mica, gypsum, calcium carbonate, apatite, synthesized silicon hydroxide hydrate; plant powders such as soy powder, wheat powder, sawdust, tabacco powder, starch powder, crystallized cellulose; polymers such as petroleum resin, vinyl chloride resin, ketone resin; alumina or beeswax etc. can be used.

As liquid carriers, alcohols such as methanol, ethanol, ethylene glycol, benzyl alcohol; aromatic hydrocarbons such as toluene, benzene, xylene, methyl naphthalene, halohydrocarbons such as chloroform, carbon tetrachloride, chlorobenzene; ethers such as dioxane, tetrahydrofuran; ketones such as acetone, methyl ethyl ketone, cyclohexanone; esters such as ethyl acetate, butyl acetate, ethyleneglycol acetate; amides such as dimethyl formamide; nitriles such as acetonitrile; ether alcohols such as ethylene glycol, diethyl ethers or water etc. can be used.

Surfactants can be advantageously employed herein such as various cationic, anionic and nonionic surfactants.

Cationic surfactants include long chain alkylammonium salts such as cetyltrimethylammonium bromide, etc.

Anionic surfactants include alkali metal, alkaline earth metal and ammonium salts of alkylarylsulfonic acids such as dodecylbenzenesulfonic acid; alkylsulfonic acids; alkylsulfuric acids such as laurylsulfuric acid; ligninsulfonic acid; arylsulfonic acids such as naphthalenesulfonic acid or dibutylnaphthalenesulfonic acid; lauryl ether sulfate; fatty alcohol sulfates; fatty acids; salts of sulfated hexadecanols, heptadecanols or octadecanois; salts of sulfated fatty alcohol glycol ethers, etc.

Examples of nonionic surfactants include condensation products of fatty alcohols such as oleyl alcohol or cetyl alcohol; phenols; alkylphenols or caster oil with ethylene oxide or propylene oxide; condensation products of naphthalene or naphthalene sulfonic acids with phenol or formaldehyde, etc.

The application amount of compound represented by the formula(1) is from 0.06 kg to 8 kg/ha, preferably from 0.25 kg to 1 kg/ha.

The active herbicidal compounds of this invention may be formulated with insecticides, fungicides, nematocides, plant growth regulators, fertilizers, other herbicides or other agricultural chemicals.

TEST: Herbicidal Activity Evaluation

The herbicidal activity test is proceeded according to the following methods.

The sterilized sandy loam soil is filled in test pot having a surface area of 348 cm$^2$ for upland test conditions or 115 cm$^2$ for paddy test species were planted in furrows.

For the pre-emergent tests, were sprayed on the soil one day after planting test compound in a mixture of acetone and 7 ml of the water containing up to 0.1% Tween 20.

The concentration of the test compound in solution was varied to give a range of application rates, generally 4.0 kg/ha and submultiples thereof. The pots were placed in a greenhouse and watered regularly at the soil surface for 21 days and herbicidal effects were visually rated by a percent control.

The pots for the post-emergent tests were placed in a greenhouse and watered for 9~14 days, then the foliage of test plants was sprayed with a solution of the test compound in a mixture of acetone and water containing a small amount of Tween 20.

After spraying the plants were kept for one day, then watered regularly for 14 to 21 days, and herbicidal activity data were recorded.

The herbicidal activity data were taken visually by percent control, wherein 0 signifies no herbicidal effect and 100 signifies complete kill.

Herbicidal activity data are shown in Table 4 and Table 5 for the compounds of the above formula(I)

TABLE 4

Herbicidal activity for upland test condition (% inhibition)

| Compound No. | Application method | kg/ha | ZEAMX | GLXMX | GOSHI | TRZAW | ORYSA | SORBI | ECHOR |
|---|---|---|---|---|---|---|---|---|---|
| 1 | PRE | 1.000 | 60 | 0 | 0 | 60 | 100 | 60 | 100 |
|  |  | 1.250 | 10 | 0 | 0 | 20 | 100 | 20 | 80 |
|  |  | 0.063 | 0 | 0 | 0 | 0 | 30 | 0 | 30 |
|  |  | 0.016 | 0 | 0 | 0 | 0 | 0 | 0 | 0 |
|  | POST | 1.000 | 100 | 60 | 50 | 100 | 100 | 100 | 100 |
|  |  | 1.250 | 100 | 20 | 40 | 60 | 100 | 60 | 100 |
|  |  | 0.063 | 30 | 0 | 30 | 40 | 50 | 20 | 100 |
|  |  | 0.016 | 0 | 0 | 0 | 30 | 0 | 0 | 60 |
| 2 | PRE | 1.000 | 100 | 0 | 0 | 80 | 100 | 100 | 100 |
|  |  | 1.250 | 40 | 0 | 0 | 20 | 60 | 30 | 100 |
|  |  | 0.063 | 0 | 0 | 0 | 0 | 0 | 0 | 40 |
|  |  | 0.016 | 0 | 0 | 0 | 0 | 0 | 0 | 0 |
|  | POST | 1.000 | 100 | 60 | 70 | 100 | 100 | 100 | 100 |
|  |  | 1.250 | 100 | 40 | 50 | 100 | 100 | 100 | 100 |
|  |  | 0.063 | 100 | 30 | 40 | 40 | 40 | 60 | 100 |
|  |  | 0.016 | 40 | 0 | 0 | 0 | 20 | 0 | 90 |
|  |  | 0.004 | 0 | 0 | 0 | 0 | 0 | 0 | 80 |
| 6 | PRE | 1.000 | 40 | 0 | 0 | 60 | 80 | 30 | 100 |
|  |  | 1.250 | 0 | 0 | 0 | 20 | 30 | 0 | 50 |
|  |  | 0.063 | 0 | 0 | 0 | 0 | 30 | 0 | 0 |
|  |  | 0.016 | 0 | 0 | 0 | 0 | 0 | 0 | 0 |
|  | POST | 1.000 | 100 | 60 | 50 | 100 | 100 | 70 | 100 |
|  |  | 1.250 | 100 | 20 | 40 | 50 | 70 | 50 | 100 |
|  |  | 0.063 | 60 | 0 | 30 | 30 | 30 | 30 | 100 |
|  |  | 0.016 | 0 | 0 | 0 | 0 | 0 | 0 | 70 |

| Compound No. | Application method | kg/ha | BROJA | DIGSA | PANDI | SOLNI | AESIN | ABUTH |
|---|---|---|---|---|---|---|---|---|
| 1 | PRE | 1.000 | 100 | 100 | 100 | 0 | 0 | 0 |
|  |  | 1.250 | 40 | 70 | 100 | 0 | 0 | 0 |
|  |  | 0.063 | 0 | 30 | 100 | 0 | 0 | 0 |
|  |  | 0.016 | 0 | 0 | 0 | 0 | 0 | 0 |
|  | POST | 1.000 | 100 | 100 | 100 | 0 | 0 | 0 |
|  |  | 1.250 | 70 | 100 | 100 | 0 | 0 | 0 |
|  |  | 0.063 | 40 | 100 | 100 | 0 | 0 | 0 |
|  |  | 0.016 | 0 | 70 | 40 | 0 | 0 | 0 |
| 2 | PRE | 1.000 | 100 | 100 | 100 | 0 | 0 | 0 |
|  |  | 1.250 | 60 | 100 | 100 | 0 | 0 | 0 |
|  |  | 0.063 | 20 | 60 | 50 | 0 | 0 | 0 |
|  |  | 0.016 | 0 | 0 | 0 | 0 | 0 | 0 |
|  | POST | 1.000 | 100 | 100 | 100 | 0 | 0 | 0 |
|  |  | 1.250 | 100 | 100 | 100 | 0 | 0 | 0 |
|  |  | 0.063 | 60 | 100 | 100 | 0 | 0 | 0 |
|  |  | 0.016 | 0 | 100 | 40 | 0 | 0 | 0 |
|  |  | 0.004 | 0 | 100 | 0 | 0 | 0 | 0 |
| 6 | PRE | 1.000 | 80 | 100 | 100 | 0 | 0 | 0 |
|  |  | 1.250 | 40 | 60 | 100 | 0 | 0 | 0 |
|  |  | 0.063 | 0 | 0 | 80 | 0 | 0 | 0 |
|  |  | 0.016 | 0 | 0 | 0 | 0 | 0 | 0 |
|  | POST | 1.000 | 100 | 100 | 100 | 30 | 20 | 30 |
|  |  | 1.250 | 70 | 100 | 100 | 0 | 0 | 0 |
|  |  | 0.063 | 30 | 100 | 100 | 0 | 0 | 0 |
|  |  | 0.016 | 0 | 60 | 40 | 0 | 0 | 0 |

TABLE 5

| | | Herbicidal activity for paddy test (% inhibition) | | | | | |
|---|---|---|---|---|---|---|---|
| Compound No. | Application (kg/ha) | ORYSA (3 Leaf) | ORYSA (seed) | ECHOR | SCPJU | MOOVA | SAGPY |
| 1 | 0.500 | 100 | 100 | 100 | 0 | 0 | 0 |
|  | 0.125 | 90 | 100 | 100 | 0 | 0 | 0 |
|  | 0.031 | 0 | 100 | 100 | 0 | 0 | 0 |
|  | 0.008 | 0 | 70 | 95 | 0 | 0 | 0 |
|  | 0.002 | 0 | 0 | 95 | 0 | 0 | 0 |
| 2 | 0.500 | 100 | 100 | 100 | 0 | 0 | 0 |
|  | 0.125 | 60 | 100 | 100 | 0 | 0 | 0 |
|  | 0.031 | 0 | 100 | 100 | 0 | 0 | 0 |
|  | 0.008 | 0 | 80 | 100 | 0 | 0 | 0 |
|  | 0.002 | 0 | 30 | 60 | 0 | 0 | 0 |
| 3 | 0.500 | 100 | 100 | 100 | 0 | 0 | 0 |
|  | 0.125 | 10 | 100 | 100 | 0 | 0 | 0 |
|  | 0.031 | 0 | 100 | 100 | 0 | 0 | 0 |
|  | 0.008 | 0 | 10 | 100 | 0 | 0 | 0 |
|  | 0.002 | 0 | 0 | 0 | 0 | 0 | 0 |
| 4 | 0.500 | 40 | 100 | 100 | 0 | 0 | 50 |
|  | 0.125 | 10 | 100 | 100 | 0 | 0 | 0 |
|  | 0.031 | 0 | 100 | 100 | 0 | 0 | 0 |
|  | 0.008 | 0 | 0 | 100 | 0 | 0 | 0 |
|  | 0.002 | 0 | 0 | 0 | 0 | 0 | 0 |
| 6 | 0.500 | 65 | 100 | 100 | 0 | 0 | 40 |
|  | 0.125 | 20 | 100 | 100 | 0 | 0 | 0 |
|  | 0.031 | 0 | 100 | 100 | 0 | 0 | 0 |
|  | 0.008 | 0 | 0 | 60 | 0 | 0 | 0 |
|  | 0.002 | 0 | 0 | 0 | 0 | 0 | 0 |
| 7 | 0.500 | 65 | 100 | 100 | 0 | 0 | 40 |
|  | 0.125 | 20 | 100 | 100 | 0 | 0 | 0 |
|  | 0.031 | 0 | 100 | 100 | 0 | 0 | 0 |
|  | 0.008 | 0 | 20 | 95 | 0 | 0 | 0 |
|  | 0.002 | 0 | 0 | 95 | 0 | 0 | 0 |
| 8 | 0.500 | 0 | 100 | 100 | 0 | 0 | 0 |
|  | 0.125 | 0 | 100 | 100 | 0 | 0 | 0 |
|  | 0.031 | 0 | 60 | 100 | 0 | 0 | 0 |
|  | 0.008 | 0 | 0 | 40 | 0 | 0 | 0 |
|  | 0.002 | 0 | 0 | 0 | 0 | 0 | 0 |
| 9 | 0.500 | 0 | 100 | 100 | 0 | 0 | 0 |
|  | 0.125 | 0 | 70 | 100 | 0 | 0 | 0 |
|  | 0.031 | 0 | 0 | 100 | 0 | 0 | 0 |
|  | 0.008 | 0 | 0 | 50 | 0 | 0 | 0 |
|  | 0.002 | 0 | 0 | 0 | 0 | 0 | 0 |
| 11 | 0.500 | 80 | 100 | 100 | 0 | 50 | 0 |
|  | 0.125 | 30 | 100 | 100 | 0 | 30 | 0 |
|  | 0.031 | 0 | 30 | 70 | 0 | 0 | 0 |
|  | 0.008 | 0 | 0 | 30 | 0 | 0 | 0 |
|  | 0.002 | 0 | 0 | 0 | 0 | 0 | 0 |
| 12 | 0.500 | 40 | 100 | 100 | 60 | 50 | 30 |
|  | 0.125 | 0 | 100 | 100 | 0 | 0 | 0 |
|  | 0.031 | 0 | 30 | 100 | 0 | 0 | 0 |
|  | 0.008 | 0 | 0 | 70 | 0 | 0 | 0 |
|  | 0.002 | 0 | 0 | 30 | 0 | 0 | 0 |
| 13 | 0.500 | 30 | 100 | 100 | 0 | 30 | 30 |
|  | 0.125 | 0 | 100 | 100 | 0 | 0 | 30 |
|  | 0.031 | 0 | 50 | 100 | 0 | 0 | 0 |
|  | 0.008 | 0 | 30 | 50 | 0 | 0 | 0 |
|  | 0.002 | 0 | 0 | 30 | 0 | 0 | 0 |
| 14 | 0.500 | 40 | 100 | 100 | 90 | 100 | 30 |
|  | 0.125 | 0 | 40 | 100 | 30 | 30 | 0 |
|  | 0.031 | 0 | 0 | 100 | 0 | 0 | 0 |
|  | 0.008 | 0 | 0 | 70 | 0 | 0 | 0 |
|  | 0.002 | 0 | 0 | 30 | 0 | 0 | 0 |
| 15 | 0.500 | 30 | 100 | 100 | 0 | 30 | 0 |
|  | 0.125 | 0 | 40 | 100 | 0 | 0 | 0 |
|  | 0.031 | 0 | 0 | 30 | 0 | 0 | 0 |
|  | 0.008 | 0 | 0 | 30 | 0 | 0 | 0 |
|  | 0.002 | 0 | 0 | 0 | 0 | 0 | 0 |
| 16 | 0.500 | 30 | 100 | 100 | 0 | 50 | 30 |
|  | 0.125 | 0 | 100 | 100 | 0 | 50 | 0 |
|  | 0.031 | 0 | 30 | 70 | 0 | 30 | 0 |
|  | 0.008 | 0 | 0 | 30 | 0 | 0 | 0 |
|  | 0.002 | 0 | 0 | 0 | 0 | 0 | 0 |
| 18 | 0.500 | 0 | 100 | 100 | 0 | 0 | 0 |
|  | 0.125 | 0 | 30 | 100 | 0 | 0 | 0 |
|  | 0.031 | 0 | 0 | 70 | 0 | 0 | 0 |
|  | 0.008 | 0 | 0 | 30 | 0 | 0 | 0 |

TABLE 5-continued

Herbicidal activity for paddy test (% inhibition)

| Compound No. | Application (kg/ha) | ORYSA (3 Leaf) | ORYSA (seed) | ECHOR | SCPJU | MOOVA | SAGPY |
|---|---|---|---|---|---|---|---|
|  | 0.002 | 0 | 0 | 0 | 0 | 0 | 0 |
| 19 | 0.500 | 0 | 30 | 100 | 0 | 0 | 0 |
|  | 0.125 | 0 | 0 | 100 | 0 | 0 | 0 |
|  | 0.031 | 0 | 0 | 80 | 0 | 0 | 0 |
|  | 0.008 | 0 | 0 | 50 | 0 | 0 | 0 |
|  | 0.002 | 0 | 0 | 0 | 0 | 0 | 0 |
| 21 | 0.500 | 100 | 100 | 100 | 0 | 70 | 0 |
|  | 0.125 | 80 | 100 | 100 | 0 | 60 | 0 |
|  | 0.031 | 0 | 100 | 100 | 0 | 50 | 0 |
|  | 0.008 | 0 | 100 | 95 | 0 | 30 | 0 |
|  | 0.002 | 0 | 20 | 40 | 0 | 0 | 0 |
| 22 | 0.500 | 100 | 100 | 100 | 0 | 60 | 0 |
|  | 0.125 | 20 | 100 | 100 | 0 | 0 | 0 |
|  | 0.031 | 0 | 100 | 100 | 0 | 0 | 0 |
|  | 0.008 | 0 | 0 | 95 | 0 | 0 | 0 |
|  | 0.002 | 0 | 0 | 0 | 0 | 0 | 0 |
| 23 | 0.500 | 60 | 100 | 100 | 0 | 0 | 0 |
|  | 0.125 | 0 | 100 | 100 | 0 | 0 | 0 |
|  | 0.031 | 0 | 100 | 100 | 0 | 0 | 0 |
|  | 0.008 | 0 | 10 | 40 | 0 | 0 | 0 |
|  | 0.002 | 0 | 0 | 0 | 0 | 0 | 0 |
| 25 | 0.500 | 50 | 100 | 100 | 0 | 0 | 0 |
|  | 0.125 | 0 | 100 | 100 | 0 | 0 | 0 |
|  | 0.031 | 0 | 60 | 100 | 0 | 0 | 0 |
|  | 0.008 | 0 | 0 | 0 | 0 | 0 | 0 |
|  | 0.002 | 0 | 0 | 0 | 0 | 0 | 0 |
| 26 | 0.500 | 30 | 100 | 100 | 40 | 0 | 0 |
|  | 0.125 | 0 | 100 | 100 | 0 | 0 | 0 |
|  | 0.031 | 0 | 20 | 100 | 0 | 0 | 0 |
|  | 0.008 | 0 | 0 | 0 | 0 | 0 | 0 |
|  | 0.002 | 0 | 0 | 0 | 0 | 0 | 0 |
| 27 | 0.500 | 0 | 100 | 100 | 0 | 0 | 0 |
|  | 0.125 | 0 | 100 | 100 | 0 | 0 | 0 |
|  | 0.031 | 0 | 0 | 50 | 0 | 0 | 0 |
|  | 0.008 | 0 | 0 | 0 | 0 | 0 | 0 |
|  | 0.002 | 0 | 0 | 0 | 0 | 0 | 0 |
| 38 | 0.500 | 100 | 100 | 100 | 0 | 0 | 0 |
|  | 0.125 | 50 | 100 | 100 | 0 | 0 | 0 |
|  | 0.031 | 0 | 100 | 100 | 0 | 0 | 0 |
|  | 0.008 | 0 | 20 | 95 | 0 | 0 | 0 |
|  | 0.002 | 0 | 0 | 0 | 0 | 0 | 0 |
| 39 | 0.500 | 80 | 100 | 100 | 0 | 0 | 0 |
|  | 0.125 | 0 | 100 | 100 | 0 | 0 | 0 |
|  | 0.031 | 0 | 100 | 100 | 0 | 0 | 0 |
|  | 0.008 | 0 | 0 | 80 | 0 | 0 | 0 |
|  | 0.002 | 0 | 0 | 0 | 0 | 0 | 0 |
| 40 | 0.500 | 0 | 100 | 100 | 0 | 0 | 0 |
|  | 0.125 | 0 | 0 | 100 | 0 | 0 | 0 |
|  | 0.031 | 0 | 0 | 0 | 0 | 0 | 0 |
|  | 0.008 | 0 | 0 | 0 | 0 | 0 | 0 |
|  | 0.002 | 0 | 0 | 0 | 0 | 0 | 0 |
| 42 | 0.500 | 0 | 100 | 100 | 0 | 0 | 0 |
|  | 0.125 | 0 | 100 | 100 | 0 | 0 | 0 |
|  | 0.031 | 0 | 20 | 80 | 0 | 0 | 0 |
|  | 0.008 | 0 | 0 | 0 | 0 | 0 | 0 |
|  | 0.002 | 0 | 0 | 0 | 0 | 0 | 0 |

The compounds of formula (I) of the present invention are used as herbicides or plant growth regulants, for example, the above compounds are suitable for selective elimination of weeds when useful plant is cultivated. Also, the compounds of formula (I) have the effect of growth inhibition and growth regulation for useful plant, for example, cereals, soybean, wheat or rice.

The compounds of formula (I) as prominent herbicides, may be applied directly to soil for pre-emergence treatment and to the plant for post-emergence treatment. The compounds of formula (I) of the present invention generally have more prominent herbicidal activity when are treated to leaves for post-emergence, and have strong safety for the broad-leaved plant, for example, soybean, cotton, sulflower, sugarbeet or vegetables. And these compounds have selectively herbicidal activity against grasses, and may be useful as herbicides in broad-leaved crops.

Certain of formula (I) compounds of the present invention especialy have prominent selectivity within the group of grasses and may be used at rate sufficient to control grass weeds in cultivated crops, for example, rice, wheat or barley, and have selectively herbicidal activity against wild grasses such as wildoat or barnyardgrass.

What is claimed is:

1. A process for the preparation of 2-methyl-2-alkylindanaldehyde of formula (7), which consists of
    preparing the 2-methyl-2-alkylindan-1,3-dione of formula (9) by reacting the benzene derivative of formula (8)

with a malonyl halide of the formula

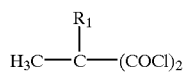

in the presence of Lewis acid;

preparing the 2-methyl-2-alkylindane of formula (10) by reduction of the above compound (9) in the presence of hydrochloric acid and zinc-mercury alloy (Zn/Hg); and reacting the compound (10) with α,α-dichloromethyl methyl ether in the presence of Lewis acid as catalyst,

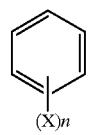 (8)

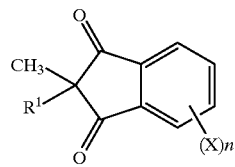 (9)

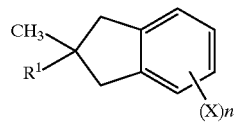 (10)

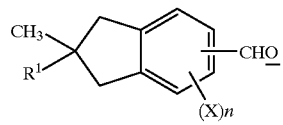 (7)

wherein

X is selected from the group consisting of hydrogen, halogen, $C_1$~$C_8$ alkyl, $C_2$~$C_6$ alkoxy, $C_1$~$C_6$ haloalkyl, nitro, $C_1$~$C_6$ alkylthio, $C_1$~$C_6$ alkylsulfinyl, $C_1$~$C_6$ alkylsulfonyl, $C_1$~$C_6$ sulfamoyl, and N,N-di($C_1$~$C_6$ alkyl) sulfamoyl;

(X)n represents the number of X substituents which may be substituted on the benzene ring, wherein n is 1, 2, or 3; and $R^1$ is selected from the group consisting of hydrogen and $C_1$~$C_6$ alkyl.

2. A process according to claim 1, wherein X is selected from the group consisting of hydrogen, halogen and $C_1$~$C_6$ alkyl; n is 1, 2, or 3; and $R^1$ is selected from the group consisting of hydrogen and $C_1$~$C_6$ alkyl.

3. A process according to claim 2, wherein X is methyl and n is 3.

4. A process according to claim 2, wherein $R^1$ is selected from the group consisting of methyl and ethyl.

5. A process according to claim 1, wherein $R^1$ is selected from the group consisting of methyl and ethyl.

* * * * *